United States Patent [19]

Parikh et al.

[11] Patent Number: 5,434,135
[45] Date of Patent: Jul. 18, 1995

[54] GROWTH FACTOR COMPOSITIONS, PREPARATION AND USE

[75] Inventors: Indu Parikh, 2558 Booker Creek Rd., Chapel Hill, N.C. 27514; Ronald Nardi, Sudbury, Mass.; Tanchum Amarant, Rehovot, Israel; Antonio Guglietta, Ann Arbor, Mich.

[73] Assignee: Indu Parikh, Chapel Hill, N.C.

[21] Appl. No.: 8,641

[22] Filed: Jan. 25, 1993

Related U.S. Application Data

[63] Continuation-in-part of Ser. No. 911,666, Jul. 8, 1992, abandoned, which is a continuation-in-part of Ser. No. 829,139, Jan. 31, 1992, abandoned, which is a continuation-in-part of Ser. No. 591,339, Oct. 1, 1990, abandoned, which is a continuation-in-part of Ser. No. 561,525, Aug. 2, 1990, abandoned.

[51] Int. Cl.$^6$ ............................................. A61K 38/00
[52] U.S. Cl. ........................................................ 514/12
[58] Field of Search ........................................... 514/12

[56] References Cited

U.S. PATENT DOCUMENTS

| | | | |
|---|---|---|---|
| 3,883,497 | 5/1975 | Gregory et al. | 260/112 R |
| 3,917,824 | 11/1975 | Camble | 514/12 |
| 4,032,633 | 6/1977 | Gregory et al. | 424/177 |
| 4,035,485 | 7/1977 | Gregory et al. | 424/177 |
| 4,490,365 | 12/1984 | Panaretto et al. | 424/177 |
| 4,528,186 | 7/1985 | Nishimura et al. | 424/99 |
| 4,621,052 | 11/1986 | Sugimoto | 435/68 |
| 4,686,283 | 8/1987 | Nestor, Jr. et al. | 530/327 |
| 4,710,473 | 12/1987 | Morris | 435/320 |
| 4,717,717 | 1/1988 | Finkehaur | 514/21 |
| 4,719,180 | 1/1988 | Eaton et al. | 435/320 |
| 4,731,357 | 3/1988 | Franklin et al. | 514/10 |
| 4,743,679 | 5/1988 | Cohen et al. | 530/350 |
| 4,760,023 | 7/1988 | Miyoshi et al. | 435/172.3 |
| 4,764,593 | 8/1988 | Banks et al. | 530/324 |
| 4,783,412 | 11/1988 | Bell | 435/240.1 |
| 4,820,690 | 4/1989 | Gregory et al. | 514/12 |
| 4,849,350 | 7/1989 | Yoshio et al. | 435/68 |
| 4,857,334 | 8/1989 | Korol et al. | 424/445 |
| 4,863,902 | 9/1989 | Amagase et al. | 514/12 |
| 4,870,008 | 9/1989 | Brake | 435/70 |
| 5,057,494 | 10/1991 | Sheffield | 514/12 |

FOREIGN PATENT DOCUMENTS

| | | |
|---|---|---|
| 63-224144 | 9/1988 | Japan. |
| 86/02271 | 4/1986 | WIPO. |
| WO90/03431 | 4/1990 | WIPO. |
| 90/10697 | 9/1990 | WIPO. |

OTHER PUBLICATIONS

*FEBS* 3962, vol. 205, No. 1, Sep. 1986, "A High Resolution $^1$H NMR Study of the Solution Structure of Human Epidermal Growth Factor", J. A. Carver, et al., pp. 77–81.

*Biochemistry*, 1988, 27, pp. 4977–4985, "Murine Epidermal Growth Factor: Structure and Function", Antony W. Burgess, et al.

*Nature*, vol. 327, May 28, 1987, "The Solution Structure of Human Epidermal Growth Factor", Robert M. Cooke, et al., pp. 339–341.

*Molecular Pharmacology*, vol. 17, No. 3, May 1980, pp. 314–320, Morley D. Hollenberg et al. "Epidermal Growth Factor-Urogastrone: Biological Activity and Receptor Binding of Derivatives".

Patent Abstracts of Japan, vol. 12, No. 306 (C-522) (3153) 19 Aug. 1988 & JP-A-6377823 (Fujisawa Pharmaceutical Co., Ltd.) 8 Apr. 1988.

*Primary Examiner*—Jill Warden
*Assistant Examiner*—Sheela J. Huff
*Attorney, Agent, or Firm*—Merchant, Gould, Smith, Edell, Welter & Schmidt

[57] ABSTRACT

The invention in growth factor compositions includes: a novel compound which is a separate pure nicked or pure non-nicked species of epidermal growth factor EGF1-48 or its hEGF1-47 or hEGF1-49 congener compound, or a pharmaceutically acceptable salt thereof; a pharmaceutical composition in dosage form comprising an effective amount of the novel compound and/or the known hEGF1-53; and use thereof for treating abnormal cell growth conditions including gastrointestinal/duodenal lesions; and methods of making the pure novel hEGF species. This unique therapeutic utility is enhanced by the unexpected and heretofore unappreciated structural stability and resistance of the pure species to enzymatic degradation.

6 Claims, 20 Drawing Sheets

```
         AAT TCC GAT AGC GAG TGT CCT CTG AGT CAC GAT GGT TAC
         Asn Ser Asp Ser Glu Cys Pro Leu Ser His Asp Gly Tyr
residue# 1                   5                  10

TGT CTA CAT GAC GGC GTC TGT ATG TAT ATT GAG GCT CTA GAC
         Cys Leu His Asp Gly Val Cys Met Tyr Ile Glu Ala Leu Asp
             15                  20                  25

AAG TAC GCG TGT AAT TGC GTT GTT GGC TAC ATC GGT TAT GAG CGT
         Lys Tyr Ala Cys Asn Cys Val Val Gly Tyr Ile Gly Tyr Glu Arg
                 30                  35                  40

TGT CAG TAT CGT GAT CTG AAA TGG TGG GAA CTT CGT TAA
         Cys Gln Tyr Arg Asp Leu Lys Trp Trp Glu Leu Arg
                     45                  48         50        53
```

FIG. 7

GROWTH FACTOR COMPOSITIONS, PREPARATION AND USE

This application is a continuation-in-part of U.S. Ser. No. 911,666 filed Jul. 8, 1992, now abandoned, which is a continuation-in-part of U.S. Ser. No. 829,139 filed Jan. 31, 1992, now abandoned, which is a continuation-in-part of U.S. patent application Ser. No. 07/591,339 filed Oct. 1, 1990, now abandoned, which is a continuation-in-part of Ser. No. 561,525 filed Aug. 2, 1990, now abandoned.

FIELD OF THE INVENTION

This invention relates to novel growth factor compositions of matter which have anti-ulcer properties. The compositions are protein-like polypeptide hormones or peptides (amino acids in a chain) which are newly found species of the epidermal growth factor (EGF) family. More particularly, the compositions comprise the novel nicked (i.e., broken chain) and non-nicked (intact chain) human EGF: hEGF1-48, and its adjacent congeners hEGF1-47 and hEGF1-49 (sometimes referred to hereinafter simply as congeners). The invention includes pure hEGF1-48 and pure congeners, hEGF1-48 and congeners in dosage form, treatment methods using hEGF1-48 and congeners, and methods of preparing pure hEGF1-48 and congeners. The invention also includes compositions comprising a therapeutically effective amount of the known hEGF1-53 in dosage form and methods using hEGF1-53 for treating certain mucosal diseases, hitherto untreated by hEGF1-53.

BACKGROUND OF THE INVENTION

Human EGF is a polypeptide of 53 amino acids with a molecular weight of approximately 6,000 daltons. The amino acid sequence is known. The known hEGF1-53 has a variety of biological/pharmacological effects including stimulation of RNA, DNA and protein synthesis; stimulation of cell growth, and inhibition of gastric acid secretion. EGF has been found to be homologous with another polypeptide hormone urogastrone. The literature occasionally identifies this peptide as EGF-urogastrone, an abstract of which, Abstract 3492, The Merck Index, 11th Ed., 552 (1989) is incorporated herewith by reference.

Patents relating to EGF, urogastrone and fragments thereof described as EGF1-47, EGF1-48 and EGF1-51 include those of Gregory et al. U.S. Pat. Nos. 3,883,497; 4,032,633; 4,035,485; and 4,820,690, and the patent of Camble et al U.S. Pat. No. 3,917,824.

Biological Activity

The known information about the biological activity of EGF has led to a consensus that human EGF1-53 is the most potent of the EGF-like moieties, with other compounds, including hEGF1-48, being less active.

EGF was initially described by Stanley Cohen and his coworkers. They observed that extracts of salivary glands from rats induced precocious eyelid opening and tooth eruption when administered to newborn rat pups. Subsequently, the peptide EGF was purified from these extracts and characterized. EGF was shown to be a potent mitogen (i.e., an agent causing or inducing mitosis or cell transformation) for a variety of cell types. EGF has both mitogenic and acid suppressive activities in the GI tract.

As indicated, EGF was isolated from salivary glands from which it is secreted into the gastrointestinal lumen (i.e., cavity or channel). It is also secreted into the GI tract from a variety of other sources. This has led to numerous attempts to characterize the activities of EGF in the GI tract.

Reports show that EGF produced a dose-dependent suppression of gastric acid secretion in dogs. Other work has confirmed this acid suppressive activity in several animal species including humans. EGF is less effective as a suppressor of gastric acid secretion than well known acid suppressive therapies such as histamine-$H_2$-antagonist or proton pump inhibitors. This suppression of gastric acid secretion follows when EGF is administered by injection (i.e., by parenteral administration) but does not follow when EGF is taken by mouth even at very high doses.

EGF administered into the gastrointestinal lumen (i.e., the stomach or other segment of the GI cavity or channel) does have trophic effects. Thus, increases in tissue mass and DNA synthesis have been reported following intragastric administration and intralumenal infusions of EGF.

The oral administration of EGF has also been shown to promote the healing of experimentally induced gastric and duodenal ulcers which have been induced by any of a variety of agents including acetic acid, laser treatment, cysteamine and indomethacin. More recently, we have found that the mechanism of action for this activity is related to the ability of EGF to accelerate the re-epithelialization (i.e., new repair growth) rate of the induced lesions (FIG. 1, described below). This is in contrast to acid suppressive therapies which appear to affect portions of the healing process that precede the re-epithelialization phase (FIG. 2).

Structure/Activity

As indicated above, human EGF is a 53 amino acid peptide which is derived as a result of cleavage from a much larger protein. EGF contains six cysteine residues which form three covalent disulfide bonds.

The structure activity relationship of EGF has been the subject of investigation by a number of laboratories. Molecular forms of EGF-like moieties include EGF1-52, EGF1-51, EGF1-49, EGF1-48, and EGF1-47, as well as a variety of chemically cleaved molecules and molecules with numerous amino acid substitutions. These molecular forms of EGF are reported to be less active than EGF1-53 with respect to mitogenic activity and receptor cell binding activity. With the exception of EGF1-52 none of the fragments of EGF has been evaluated for its in vivo activity, probably owing in each case to the prevailing opinion that it would be less efficacious than EGF1-53. Although these molecular forms have been published as having been isolated, none with the possible exception of EGF1-52 has been purified to homogeneity and characterized for homogeneity and identity.

SUMMARY OF THE INVENTION

The present invention is based on the discovery of the pure human EGF (hEGF) species, i.e., species each purified to homogeneity:
  non-nicked (or intact chain) polypeptides EGF1-47, EGF1-48, and EGF1-49; and
  nicked (or broken chain) polypeptides EGF1-47, EGF1-48, and EGF1-49.

The invention is thus based on the discovery that conventional means of obtaining EGF1-48 and its congeners EGF1-47 and EGF1-49—such as by chemical synthesis, limited proteolysis of intact EGF, and recombinant microbial techniques—do not produce the EGF species alone but rather produce the mixed species of the hitherto unnoticed comigrant nicked and non-nicked mixture which by conventional methods including chromatographic techniques have prior to the present invention never been isolated as the separate pure nicked and pure non-nicked species (FIG. 3).

The invention thus provides the nicked and non-nicked forms of human EGF1-48 and its adjacent EGF1-47 and EGF1-49 congeners also in nicked and non-nicked forms (each as a discrete and separate novel molecular entity). These compounds have unexpected therapeutic utility for the treatment of gastrointestinal lesions in general and of hypersecretory conditions both for inhibition of gastric acid secretion (GAS) and for treatment where GAS is a real or potential problem such as in cases of stress ulcerations, gastric ulcers, and duodenal ulcers. Thus, hEGF1-48 and its adjacent congeners in pure nicked form or pure non-nicked form, each possess unique and unexpected activity. The compounds not only afford inhibition of GAS but also stimulate proliferation of gastrointestinal mucosa.

It is also found that, unlike EGF1-53, pure EGF1-48 and its pure congeners each in either nicked or non-nicked form have structural stability and resistance to enzymatic degradation (gastric juice and trypsin) which stability and resistance (especially when the compounds are orally administered) result in unexpected utility for treating gastrointestinal lesions.

BRIEF DESCRIPTION OF THE DRAWINGS

FIG. 7 is a gene design diagram for hEGF1-48; showing the nucleotide and corresponding amino acid sequence for the EGF coding region of the EGF expression cassette inserted in the P. pastoris strains; for the strain containing only the hEGF1-48 coding region, the nucleotides coding for residues 49-53 were not included in the cassette;

DETAILED DESCRIPTION AND PREFERRED EMBODIMENTS

The invention in one aspect comprises a polypeptide selected from hEGF1-48 or its adjacent congener or a pharmaceutically acceptable salt thereof, which polypeptide is pure non-nicked or pure nicked, preferably a polypeptide which is non-nicked, and preferably EGF1-48 of the formula I:

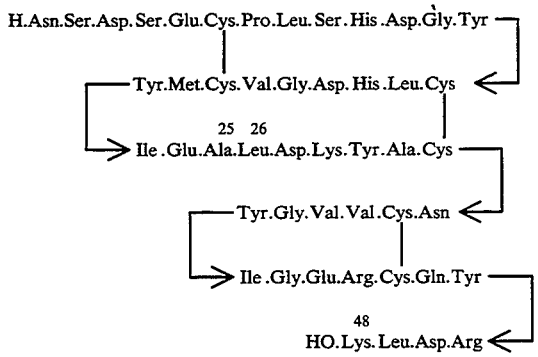

I

A preferred salt is the trifluoroacetate salt or the acetate salt. The term hEGF1-48 used herein refers to the intact (i.e., the non-nicked form) unless otherwise specified.

Also preferred is a polypeptide of the formula I which is nicked EGF1-48 or its nicked adjacent congener or a pharmaceutically acceptable salt thereof, more particularly or preferably nicked between at least the 25position of the polypeptide chain.

Figure 4:
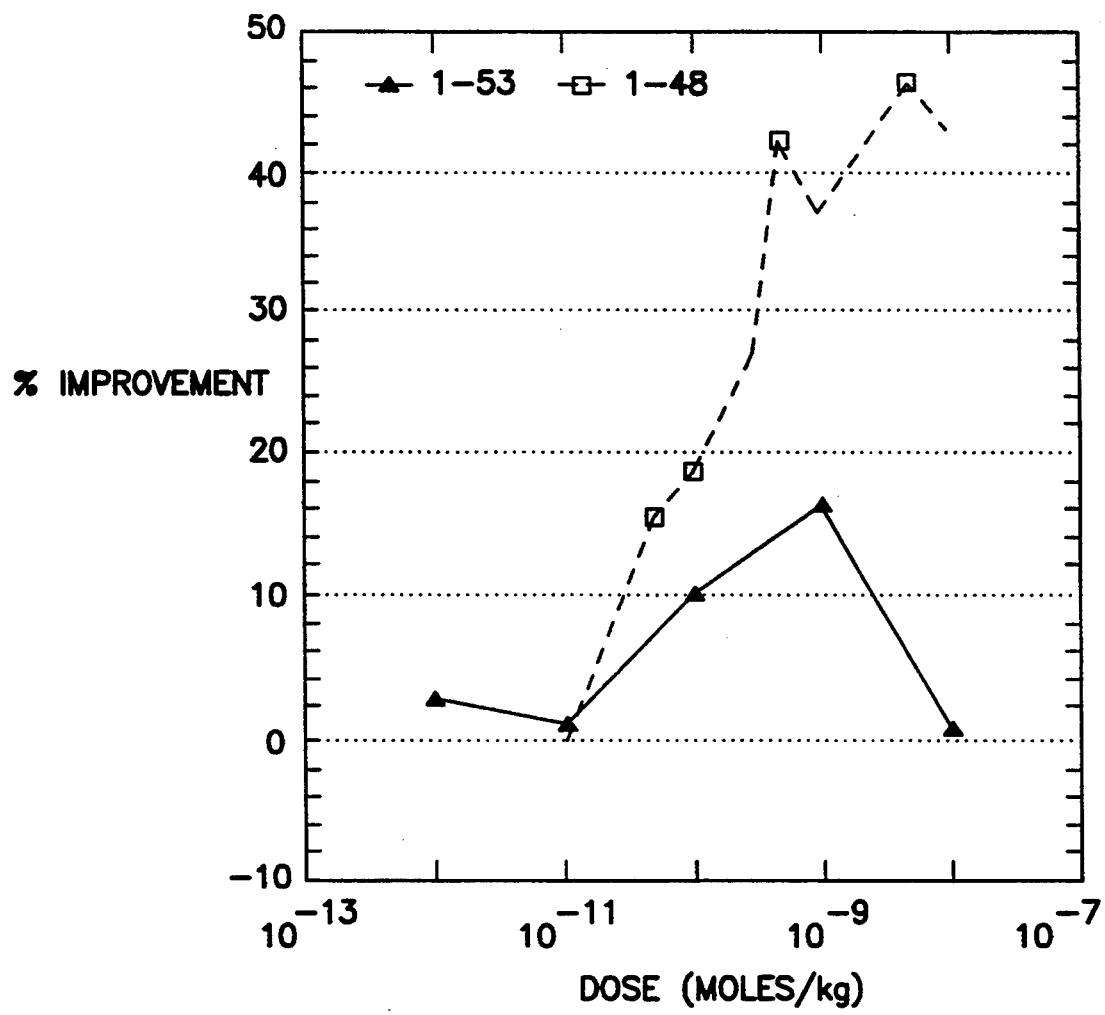
FIG. 4 is a graph of the dose effect of EGF, relative to the dose effect of hEGF1-48, on indomethacin-induced gastric lesions in the rat, expressed as percent improvement compared to the saline group; rats received an injurious dose of indomethacin (orally) and either saline or the indicated dose (orally) of EGF or hEGF1-48. At 12 hours post dosing, animals were sacrificed and the extent of gastric damage assessed.
Figure 5A:
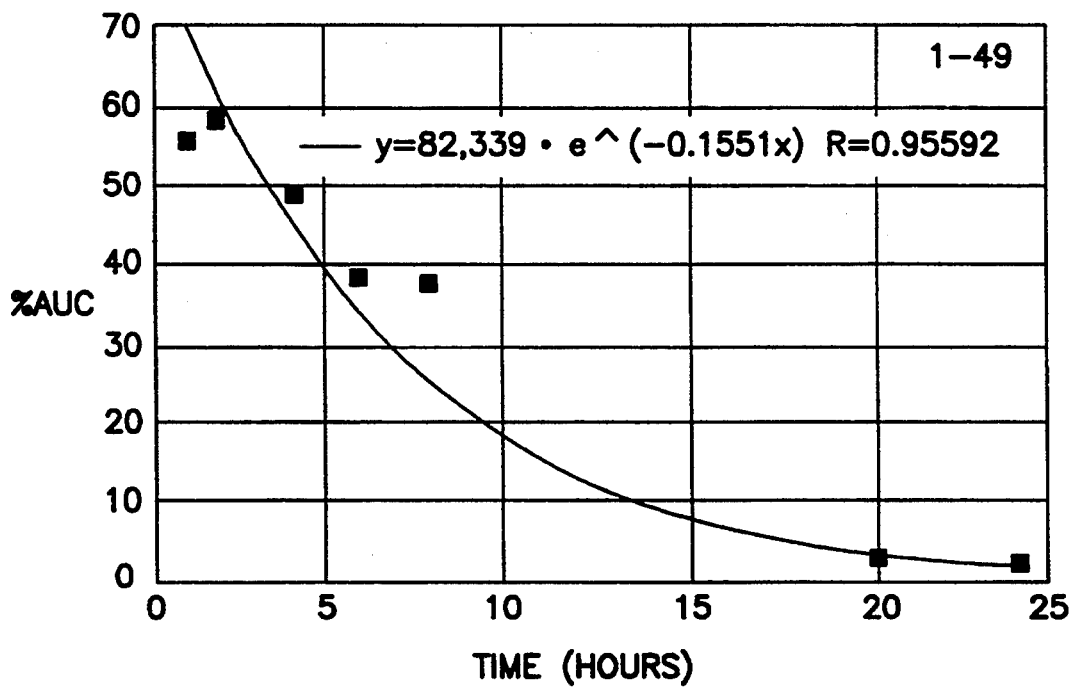
FIGS. 5A-5C are 3-graphs comparing the % AUC for EGF1-49, EGF1-48, and EGF, respectively; samples of each parent peptide, dissolved in human gastric juice were incubated at 37° C. At the indicated times aliquots were withdrawn and the amount of intact parent peptide was determined as the area under the curve (AUC) of the $A_{214}$ (absorbance at 214 nanometers) chromatogram.
Figure 5B:
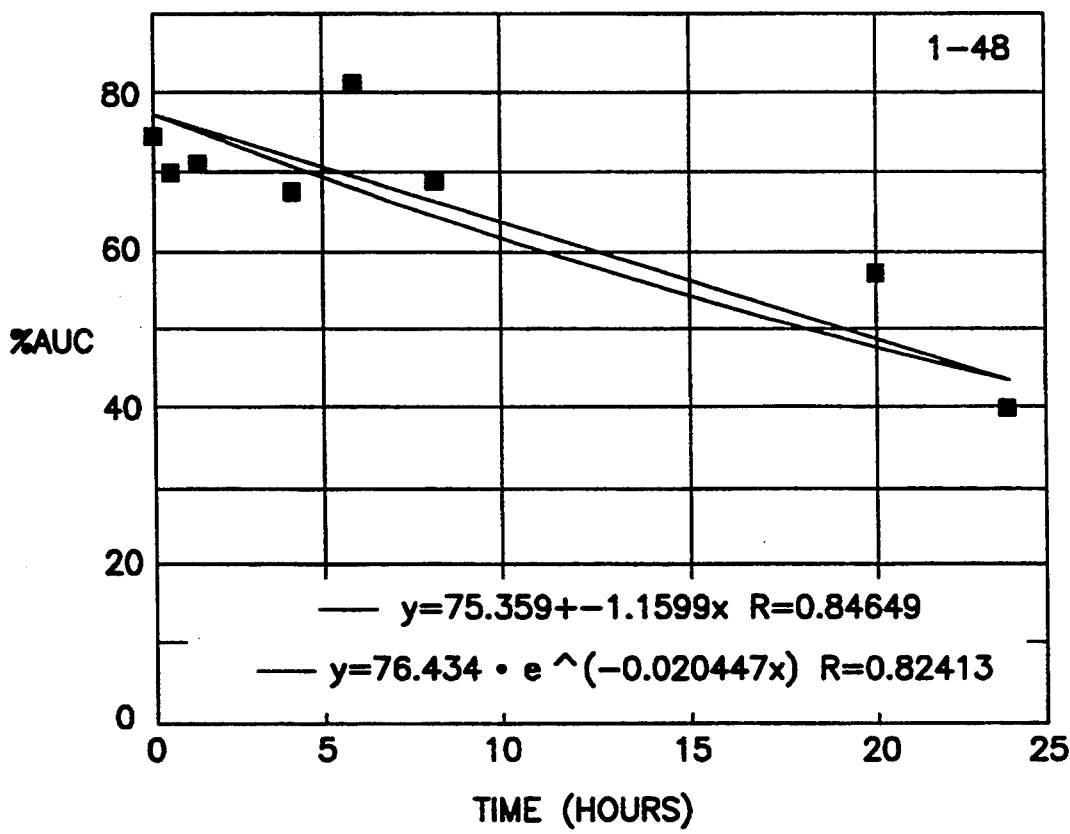
Figure 5C:
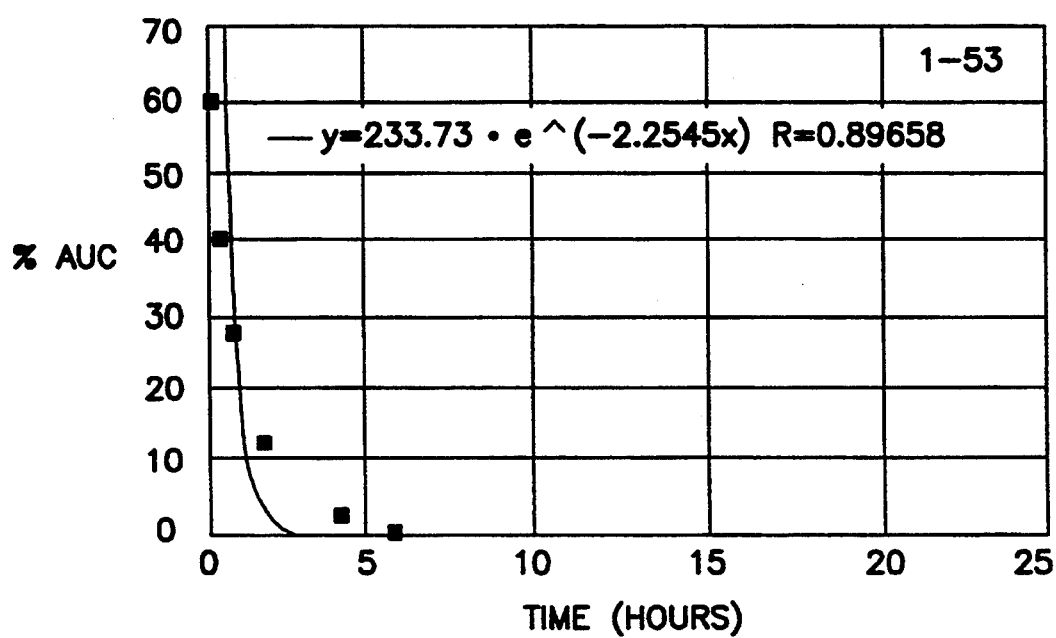
Figure 6:
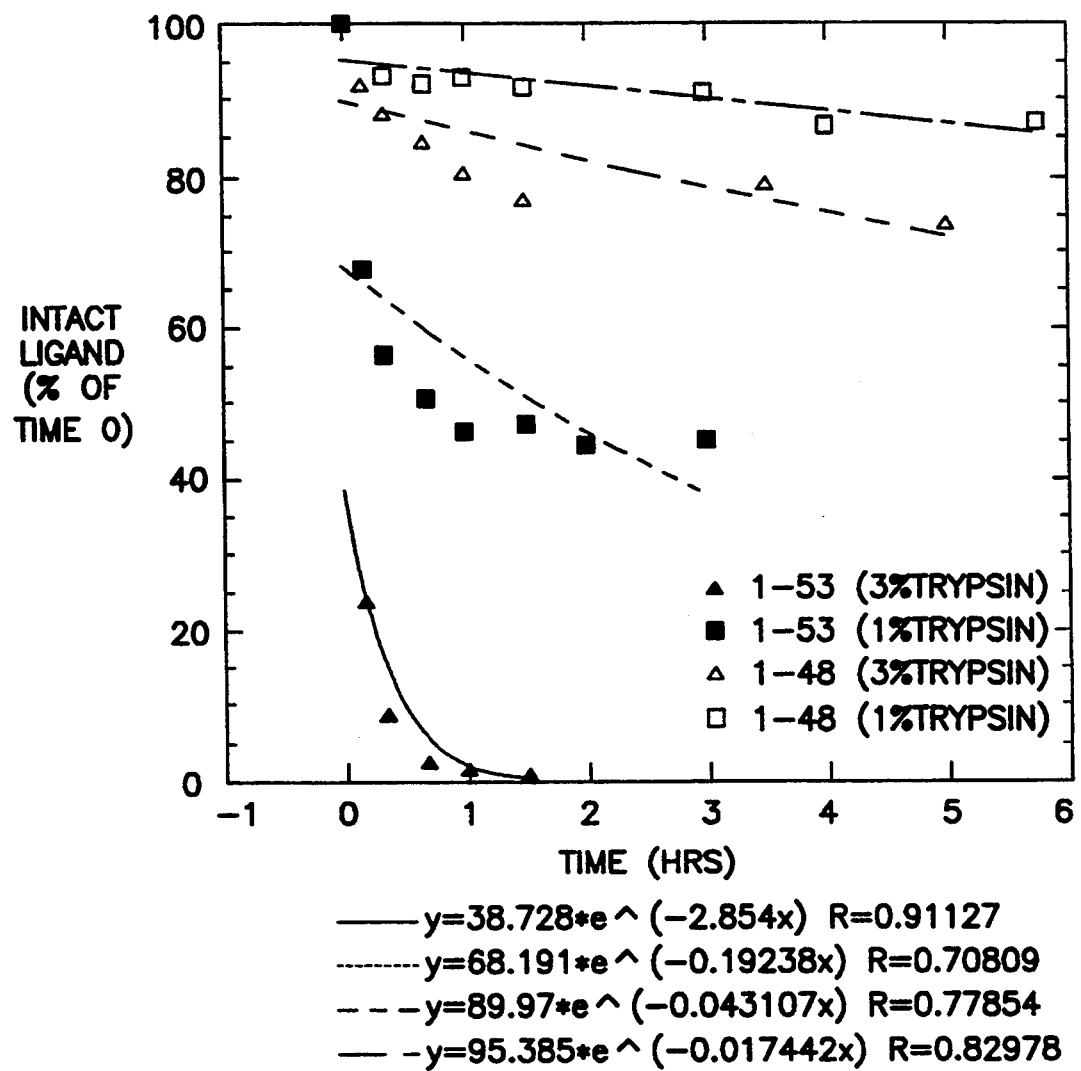
FIG. 6 is a composite graph showing over time the relative percentages of unhydrolyzed EGF (hEGF1-48 and EGF1-53) in 1% and 3% trypsin; the experiment is the same as described in FIG. 5 except trypsin is the enzyme source.

We have found that hEGF1-48 is surprisingly more effective than hEGF1-53 in the treatment of experimentally induced lesions in the gastrointestinal tract (FIG. 4). A typical result, for example, in the treatment of indomethacin-induced lesions in the rat was an apparent modest reduction (16%) in lesion size (read after 12 hours) in the use of hEGE1-53 at a zero time oral dose of 1.0 nanomoles per Kg. (but without reduction at higher dosage). The size reduction observed was however not statistically different from controls. A typical result in the comparable use of intact hEGF1-48 at various oral doses (0.5, 1.0, 5.0, and 10.0 nmol per Kg) varied from 37 to 46% improvement in lesion size reduction read at 12 hours versus controls, a result that was found to be significant based on t-test analysis. This unique therapeutic utility is enhanced by the unexpected and heretofore unappreciated structural stability and resistance, as indicated, to enzymatic degradation of nicked and non-nicked EGF1-48 and its congeners. The time course of degradation of pure intact (non-nicked) hEGF1-48, for example, in gastric fluid was found in the typical case to be only slight at one hour, slight to moderate at four hours, and marginally more degraded at 19 hours (FIG. 5). By contrast, the comparable time course of hEGF1-53 was approaching almost complete degradation at one hour. Similarly, the time course of degradation of intact hEGF1-48 in 1% or 3% trypsin (w/w) was ca. 10% and ca. 25% respectively after four hours. By contrast, the comparable time course of degradation of hEGF1-53 in 1% and 3% trypsin was ca. 50% after one hour and 90-100% after one hour, respectively (FIG. 6).

As used herein, the term "pharmaceutically acceptable salt" refers to a salt that retains the desired biological activity of the parent compound and does not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein in reference to the EGF species, the term "non-nicked" means the intact polypeptide in which the three disulfide bonds are intact or unbroken and the polypeptide chain is intact. The term "nicked" means that the three disulfide bonds are intact and the polypeptide chain is nicked, i.e., broken, between at least one pair of adjacent residues of the polypeptide chain such as the 25-26 pair of residues.

The invention in another aspect comprises pharmaceutical compositions in dosage form, preferably for oral, intravenous or topical administration, containing an effective amount of the described polypeptide (which may be the nicked or non-nicked hEGF1-48 or its nicked or non-nicked adjacent congener hEGF1-47 or hEGF1-49 or may be hEGF1-53) and a pharmaceutically acceptable diluent or carrier, for the prevention or management or treatment suitably by the enteral or parenteral routes of mucosal diseases, especially of the gastrointestinal mucosa such as erosive or inflammatory diseases in a subject. The compositions can be used in the form of pharmaceutical preparations comprising each such polypeptide compound in a pharmacogically effective amount in admixture with a pharmaceutically acceptable carrier which may be conventional per se. These preparations may be formulated by well known procedures. In these respects, see for example *Remington's Pharmaceutical Sciences,* Chapter 43, 14th Ed., Mack Publishing Co., Easton, Pa. 18042, USA. These preparations can be administered in any suitable way such as orally, e.g. , in the form of tablets, dragees, capsules, solutions, or emulsions, or parenterally, e.g., in the form of injectable solutions at suitable pH, or topically, e.g., in the form of a cream. In one preferred aspect of the invention, the polypeptide of the mentioned pharmaceutical compositions is the known hEGF1-53 or salt thereof which it is found is less stable than hEGF1-48 and thus for its pharmacologic effect becomes degraded in vivo to hEGF1-48. Methods for producing hEGF1-53 including recombinant methods are known. One uses an amount of the polypeptide (hEGF1-48 or congener, or hEGF1-53, or salt thereof) that is effective to prevent or manage the disease in the subject or to promote the management or healing thereof. For human treatment, the non-nicked hEGF1-48 or hEGF1-53 is to be administered in a dosage regimen, preferably oral, intravenous, or topical. The oral or intravenous regimen is administered in pharmacologic amounts between about 0.001 nanomoles/kg and at least about 100 nanomoles/kg per day in pharmaceutically acceptable dosage form. The regimen for nicked hEGF1-48 or congener in oral or intravenous dosage form requires a higher dosage in an amount ranging from about 0.01 nanomoles/kg to at least about 10 micromoles/kg per day. Treatment of GI disease conditions may be achieved by the oral route without inhibiting gastric acid secretion in the subject. In orally administered hEGF1-48, doses which are lower than the doses required to affect gastric acid secretion, have significant efficiency for the healing of mucosal lesions. The invention contemplates for hEGF1-48 and its congeners pharmaceutical compositions for the prevention or management of or treatment for inflamed, erosive or atrophic mucosal disease conditions such as erosive esophagitis, ulcerative esophagitis, inflammatory bowel disease, duodenal ulcers, gastric ulcers, esophageal ulcers, duodenitis, gastritis, atrophic gastritis, nonsteroidal anti-flammatory drug-induced mucosal injury, mucositis, mouth ulcers, aphthous ulcers, ulcerative colitis, Chrohn's disease, hypersecretion, inflamed, erosive or atrophic conditions of the small and large intestine, total parenteral nutrition (TPN) induced mucosal atrophy, erosive conditions of the GI mucosa, pancreatitis, regeneration of pancreatic tissue, islet cell regeneration, liver regeneration after partial hepatectomy, diverticulitis, hepatitis, necrosis due to microbiologic infection such as for example due to liver disease associated with necrosis of hepatic tissue, kidney disease associated with necrosis of kidney tissue; and the like.

The invention contemplates for hEGF1-53 pharmaceutical compositions for the treatment of the aforesaid disease conditions excepting duodenal ulcers, gastric ulcers, hypersecretion and liver regeneration after partial hepatectomy. The aforesaid necrosis of either hepatic tissue or kidney tissue is defined more particularly for purposes of the invention as a necrosis due to microbiologic infection such as vital hepatitis, tuberculosis, typhoid fever, tularemia, brucellosis, yellow fever, and the like, or necrosis due to ischemic injury resulting from shock, heart failure, and the like, or necrosis due to acute or chronic reaction with drugs and toxic substances such as chloroform, carbon tetrachloride, phosphorous poisoning, and the like. In a preferred embodiment of an oral dosage form and use thereof, an appropriate amount of nicked or non-nicked hEGF1-48 or an adjacent congener (as the case may be) or hEGF1-53, in non-salt or salt form, is dissolved in aqueous solution, which may include a water soluble cellulose stabilizer such as described in U.S. Pat. No. 4,717,717, incorporated herewith by reference, and administered orally. Other oral dosage forms described herein can also be used.

Nicked or non-nicked hEGF1-48 or an adjacent congener or hEGF1-53 may be administered therapeutically as part of a common oral formulation which includes a known anti-ulcer agent.

Examples of such anti-ulcer agents known in the art are: the so-called histamine H-2 receptor antagonists, e.g. cimetidine, ranitidine, and famotidine; gastric specific anti-cholinergic agents such as pirenzepine; prostaglandin E2 analogues such as misoprostol or arboprostil; agents such as sucralfate or carbenoxolone; proton pump inhibitors such as omeprazole; and antacids such as aluminum hydroxide/magnesium hydroxide mixtures. For a layman's description of these and other drugs, see *Joe Graedon's The New People's Pharmacy*, Chapter 5, 134–163, 1985. Bantam Books, Inc., New York, incorporated herein by reference.

The known anti-ulcer agent may be present in the composition in an amount consistent with its known therapeutic activity. Thus, for example, an oral composition containing cimetidine may contain between 100 and 1000 mg. of cimetidine.

The oral pharmaceutical composition may be formulated by means known to the art in the form of, for example, aqueous or oily solutions or suspensions, emulsions, tablets, capsules, lozenges, chewing gums or dispersable powders.

A preferred intravenous formulation is one provided in a vial containing pure hEGF1-48 or its pure congener or hEGF1-53 (50 micrograms/ml.), surfactant (Polysorbate-80, 0.1 mg/ml.), and water to make 1 ml. in a buffered system (e.g., PBS) at pit 6.

In another aspect, the invention comprises a method for prevention or management or treatment of diseases of the gastrointestinal mucosa including erosive or inflammatory diseases in a subject which comprises administering to the subject an amount of nicked or non-nicked hEGF1-48 or its adjacent congener or hEGF1-53, or a pharmaceutically acceptable salt thereof that is effective to prevent or manage the disease in the subject or to promote the management or healing thereof. For human treatment, the non-nicked pure hEGF1-48 or hEGF1-53 is to be administered in a dosage regimen, preferably oral or intravenous, in pharmacologic amounts between about 0.001 nanomoles/kg and at least about 100 nanomoles/kg per day in pharmaceutically acceptable dosage form. The regimen for nicked EGF1-48 or congener requires a higher dosage in an amount ranging from about 0.01 nanomoles/kg to at least about 10 micromoles/kg per day. Treatment of GI disease conditions may be achieved by the oral route without inhibiting gastric acid secretion in the subject. The invention contemplates for hEGF1-53 treatment of the aforesaid disease conditions specified for hEGF1-53.

In still another aspect the invention concerns a method of making non-nicked hEGF1-48 comprising the steps of:

A. growing a human EGF expression strain of the methylotrophic yeast *P. pastoris* in a fermentation growth medium having a methanol feed, at acid pH, preferably pH 5, for a methanol-sustained growth period resulting in the selectively induced formation of a mature growth medium broth containing yeast expressed non-nicked or intact hEGF1-48 and excluding nicked hEGF1-48, and B. separating the hEGF1-48 from the broth by means excluding other proteins, especially EGF species other than hEGF1-48, which means excluding other proteins preferably may include first treating the mature broth with trypsin to selectively degrade the other proteins while leaving intact the hEGF1-48, employing, for example, 1 to 3% trypsin in the broth for one hour at 37° C., followed by PLC chromatography.

The fermentation is carried out at an acid pH, preferably at pH 5. The methanol feed portion of the fermentation (as described elsewhere herein) is maintained for about 24 to about 40 hours, more preferably for optimum production, about 36 hours. Under these conditions of relatively short methanol induction, we have found surprisingly that the sole EGF product expressed in the broth is the desired non-nicked hEGF1-48. We have found, however, that when the methanol feed portion of the fermentation is carried out for substantially longer periods, i.e., a long methanol induction period (e.g., more than 40 hours), a mixture of both products is obtained: non-nicked hEGF1-48 and nicked hEGF1-48. This result is exemplified by the following methanol-sustained incubation runs, which are typical:

TABLE I

| Broth No. | Incubation Time in MEOH | % Nicked |
|---|---|---|
| 477 | 110 hrs | 50.3 |
| 490 | 40 hrs | 2.7 |

The method employing the short methanol induction is preferred because it facilitates the workup and purification of the desired non-nicked hEGF1-48 in non-salt or salt form. The separation of non-nicked hEGF from the broth may be carried out by art-recognized means.

In still another aspect, the invention concerns a method of making hEGF comprising the steps of:

A. growing a human EGF expression strain of the methylotrophic yeast *P. pastoris* in a fermentation growth medium having a methanol feed for a methanol-sustained growth period resulting in the formation of a mature growth medium broth containing a mixture of yeast expressed non-nicked hEGF and nicked hEGF, B. isolating the hEGF mixture from the broth by steps comprising subjecting the hEGF to column chromatography comprising adsorption on and elution from a strong cation exchange resin under acid conditions to cause the non-nicked hEGF and the nicked hEGF to be eluted as separate eluates respectively, and C. isolating the non-nicked hEGF and the nicked EGF from the respective eluates. Preferably, the period of methanol-sustained growth is substantially longer than 40 hours, up to 100 hours or longer, as desired, to produce a sufficient quantity of nicked hEGF in the broth mixture.

Figure 1:
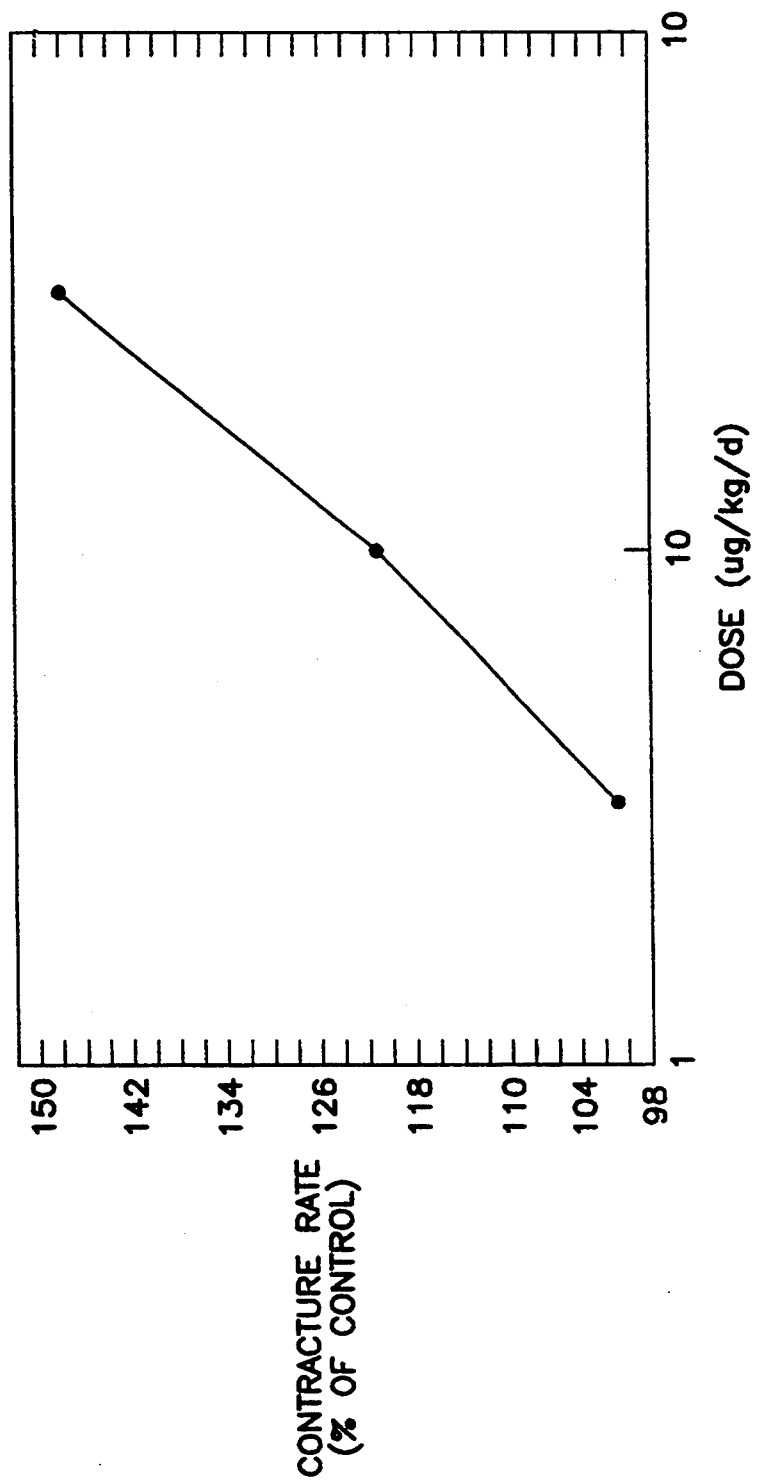
FIG. 1 is a graph showing the dose response of EGF expressed as contracture rate in treatment of canine gastric ulcer; ulcers were induced via laser of the antrum. The ulcer healing process was followed by repeated endoscopic examination during which images of the lesion were obtained. For each animal, lesion sizes were measured and the rate of reepithelialization was determined as the rate constant for a least squares fit of the lesion sizes over the time course of the experiment.
Figure 2:
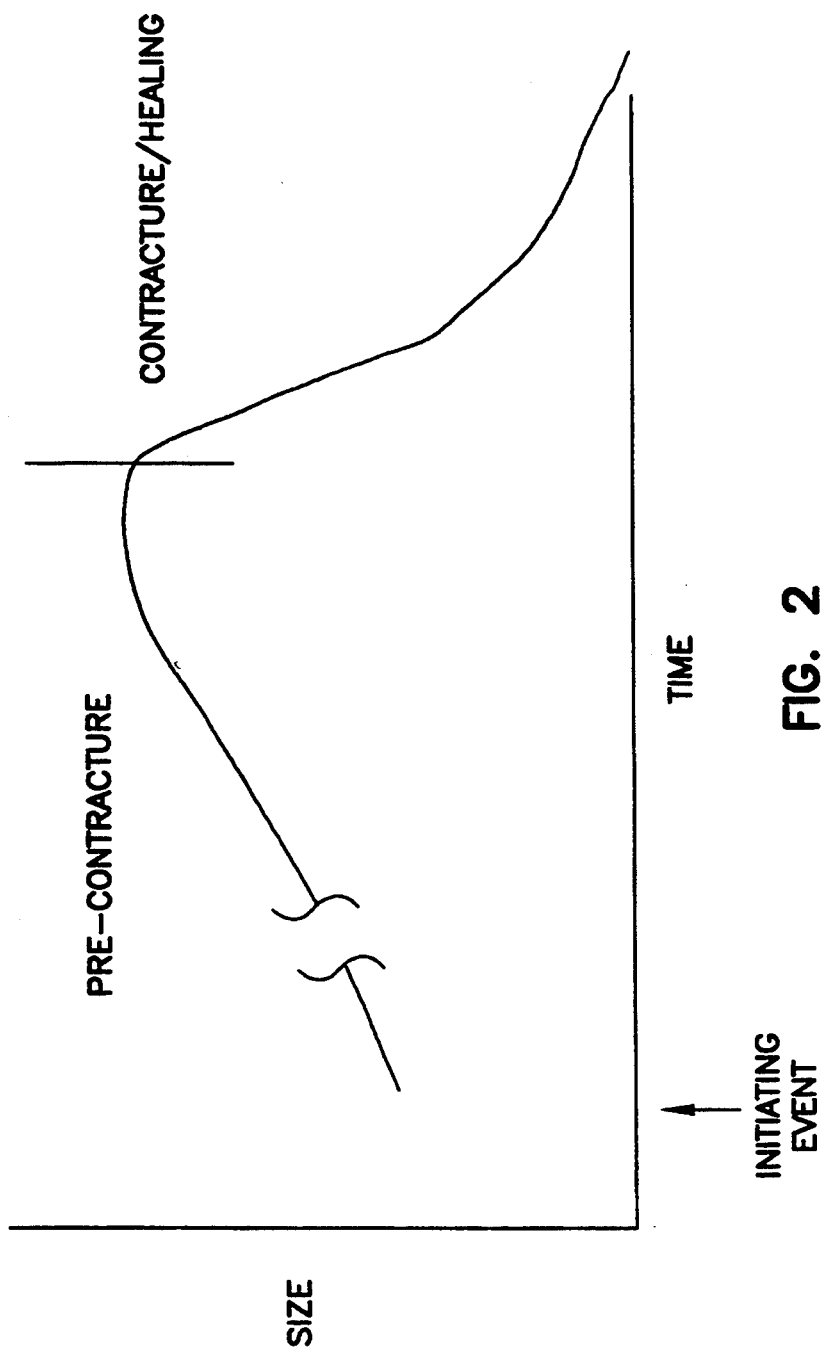
FIG. 2 is a schematic of the ulcer phases showing the variation in ulcer size following the initiating event and during pre-contracture, contracture and healing.
Figure 3:
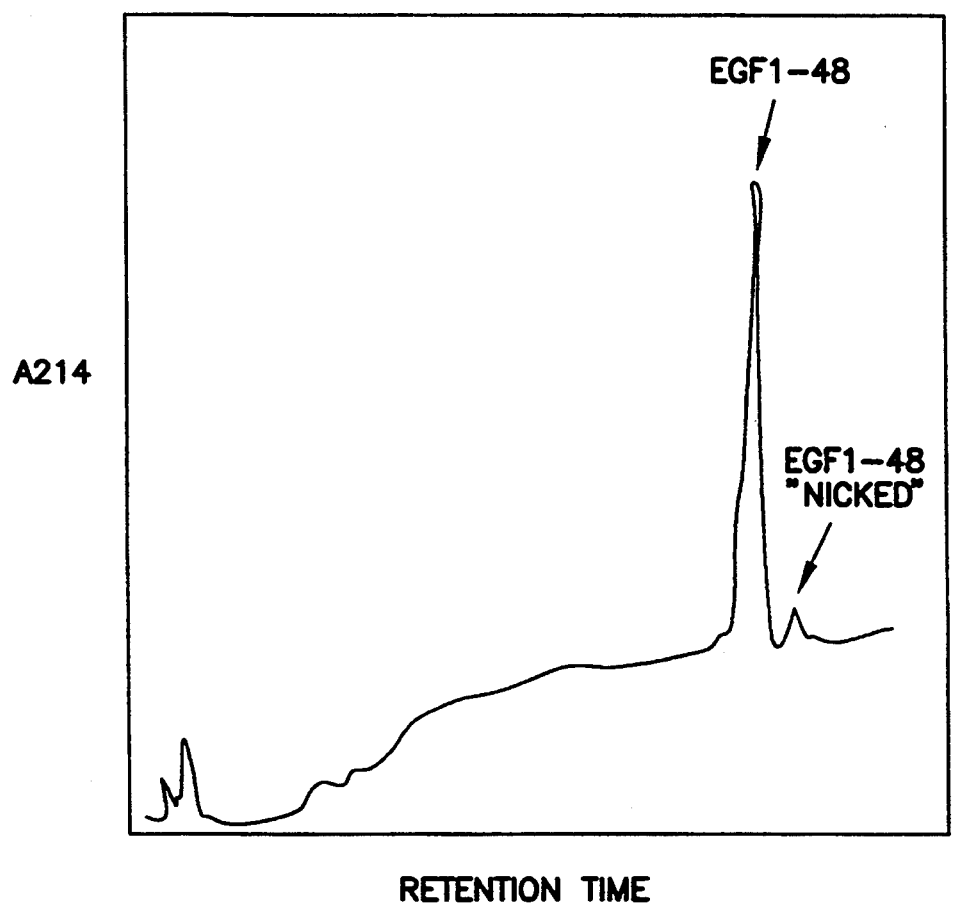
FIG. 3 is a plot of the chromatographic separation profile over time of the hEGF1-48 eluting first as the non-nicked (intact) species and then as the nicked species; the EGF1-48 fraction was isolated and purified from the broth of a fermentation during which expression was induced. This representative chromatogram demonstrated an additional chromatographic separation of the purified hEGF1-48 into the nicked and intact species using an ion exchange resin as described within.

A preferred resin for column chromatography is a sulfoethylaspartamide resin. We have found surprisingly that while intact and nicked hEGF1-48 have the same retention time on reversed phase HPLC columns, they can be separated on the strong cation exchange column under acidic conditions (FIG. 3). Under these conditions, nicked EGF1-48 has one extra positive charge as compared with intact EGF1-48. The preferred column is a column of suitable dimension preferably measuring 4.6×200 mm., 300 Angstrom units, 5 microns, employing sulfoethylaspartamide-SCX (available from the Nest Group). For elution, the preferred mobile phases are mobile phase A comprising five millimolar phosphoric acid titrated to pH 3 with KOH and containing 25% acetonitrile and mobile phase B comprising mobile phase A that contains 0.3 molar KCl. The preferred elution conditions comprise a linear gradient from phase A to 70% phase B over 45 minutes at 1 ml. per minute. The nicked EGF elutes after the non-nicked EGF and the eluate containing it is lyophilized in pure form. It is nicked between residues 25 and 26 and was found by protein sequencing to be totally nicked. The non-nicked EGF is obtained separately in pure form by lyophilizing the eluate containing it. The invention contemplates the production of any of the species: EGF1-48, EGF1-47, and EGF1-49 by appropriate selection of the producing yeast strain which strain is known or is available by art-recognized means.

Another aspect of this invention is the production of hEGF1-49. The present preferred method includes the steps comprising:

A. Enzymatically treating EGF1-53 by suitable means such as treating with human gastric juice, carboxypeptidase or the like, preferably using human gastric juice as the source of enzyme, for a time sufficient to convert most of the starting material to EGF1-49, about two hours at 37° C. in gastric juice; and B. Separating, preferably by chromatographic procedures, the EGF1-49 from other materials in the reaction mixture. The enzyme reaction may be stopped or quenched by a variety of means including but not limited to: addition of alcohol or other organic solvent, adjustment of pH above 3.0, or immersion of the reaction vessel in an ice cold bath to reduce the temperature. In the currently preferred embodiment, the chromatographic procedures described for the isolation of EGF1-48 also have been used effectively to purify EGF1-49.

In yet another aspect the invention concerns a method of making hEGF1-47 comprising the steps of:

A. growing a human EGF expression strain of the methylotrophic yeast *P. pastoris* in a fermentation growth medium having a methanol feed, at acid pH, preferably pH 5, for a methanol-sustained growth period resulting in the selectively induced formation of a mature growth medium broth containing yeast expressed non-nicked or intact hEGF1-47, and B. separating the hEGF1-47 from the broth by means excluding other proteins, especially EGF species other than hEGF1-47, which means excluding other proteins preferably may include first treating the mature broth with trypsin to selectively degrade the other proteins while leaving intact the hEGF1-47, employing, for example, 1 to trypsin in the broth for one hour at 37° C., followed by HPLC chromatography. In the currently preferred embodiment, the chromatographic procedures described for the isolation of EGF1-48 also have been used effectively to purify EGF1-47.

The fermentation is carried out at an acid pH, preferably at pH 5. The methanol feed portion of the fermentation (as described elsewhere herein) is maintained for about 24 to about 40 hours, more preferably for optimum production, about 36 hours.

As indicated, the nicked and non-nicked EGF1-48 and congeners are for purposes of the invention preferably derived recombinantly by microbial methods, i.e., by rDNA techniques.

EGF Products By Recombinant Technology

The knowledge of the amino acid sequence of urogastrone allowed design and construction of synthetic genes encoding this peptide, which in turn allowed development of recombinant expression systems. By 1982, the first recombinant expression system for hEGF was reported, utilizing the bacterium *E. coli* to produce hEGF and yielding 2.3 mg/l of biologically active material. Later, the use of the *S. cerevisiae* α-mating factor leader sequence to direct secretion of hEGF from *S. cerevisiae* increased the expression level of a (1-52) form of hEGF to 5 mg/l. More recently, an improved Bacillus expression host has been reported to secrete 240 mg/l of hEGF with no appreciable degradation. With the exception of the Bacillus system, for which no published information on productivity during scale-up is available, expression levels of hEGF in these recombinant systems are low.

The methylotrophic (requiring methyl alcohol as a nutrient) yeast, *Pichia pastoris*, has been developed as an improved host for production of recombinant products. Recombinant *Pichia pastoris* strains advantageously can secrete recombinant proteins in the gram per liter range, can adapt to batchwise or continuous cultivation, have an extremely stable recombinant phenotype (i.e., physical, biochemical and physiological makeup of the yeast), and can maintain high yields over several orders of fermentation scale-up.

What follows is a description of the development and scale-up including the best mode according to the invention to a pilot-plant scale of a process for production and purification of bioactive hEGF, for illustrative purposes usually as the EGF1-48 species that is secreted into the growth medium of a recombinant strain of *P. pastoris*.

A. Expression and Biochemical Analysis of hEGF Secreted by *Pichia pastoris*

The alcohol oxidase (AOX1) promoter used to drive heterologous (i.e., different species) peptide synthesis in *P. pastoris* expression systems is derived from the primary alcohol oxidase gene. Alcohol oxidase catalyzes the oxidation of methanol to formaldehyde and hydrogen peroxide as the first step in methanol metabolism. Development of a fermentation protocol which induces expression of AOX1-regulated heterologous genes has been previously described.

Briefly, the fermentation consists of three distinct stages. First, the cells are grown on glycerol to accumulate cell biomass while repressing heterologous gene expression. Second, glycerol is fed at a rate which keeps yeast cell growth carbon-limited; the cell mass increases further during this stage but the carbon limitation allows derepression of the methanol metabolic pathway so that the cells begin to adapt to growth on methanol. In the third stage, full expression of the heterologous peptide is induced by introduction of a methanol feed. This protocol was used to induce expression of hEGF from three recombinant strains.

Two *P. pastoris* strains are designated G+EGF817S1 and G+EGF819S4. They contain two and four copies, respectively, of an hEGF expression cassette coding for EGF1-53 integrated into the AOX1 locus of the host strain GS115. A third strain G+EGF206S10 contains six copies of an hEGF cassette coding for EGF1-48 integrated at the H1S4 locus of the host strain GS115. Each expression cassette contains the *P. pastoris* alcohol oxidase (AOX1) promoter and regulatory sequences, DNA sequences coding for the *S. cerevisiae* α-mating factor prepro leader sequence fused to a synthetic gene encoding respectively for hEGF1-53, hEGF1-53, and hEGF1-48 (FIG. 7); and the AOX1 transcription termination sequence. The transforming DNA also includes the *P. pastoris* HIS4 sequence.

HPLC was routinely used to quantitate the various hEGF species present in cell-free broth from fermentations of strain G+EGF819S4. At the smaller fermentation scales, a series of HPLC profiles typically was taken over 36 hours following methanol induction of EGF expression. At the earliest times a single peptide peak appeared on the chromatogram. By seven or eight hours into the methanol induction phase a second peak was evident and represented the major species present. After 36 hours of methanol induction, a single major peak, which eluted appreciably earlier in the gradient than the two peaks seen previously, was evident. Mass spectral analysis and amino acid analysis identified the three peaks as EGF1-52, EGF1-51, and EGF1-48, respectively. Thus, the EGF was being converted to a progressively shorter peptide over time. We found that the conversion of hEGF from the EGF1-52 to the EGF1-48 form was pH dependent. The conversion pattern described above occurred when the fermentation preferably was conducted at pH 5.

Only one hEGF species, non-nicked hEGF1-47, was produced by strain G+EGF206S10. This strain contains six copies of a DNA sequence encoding hEGF1-48.

B. Biological Activity of hEGF1-48

Figure 8:
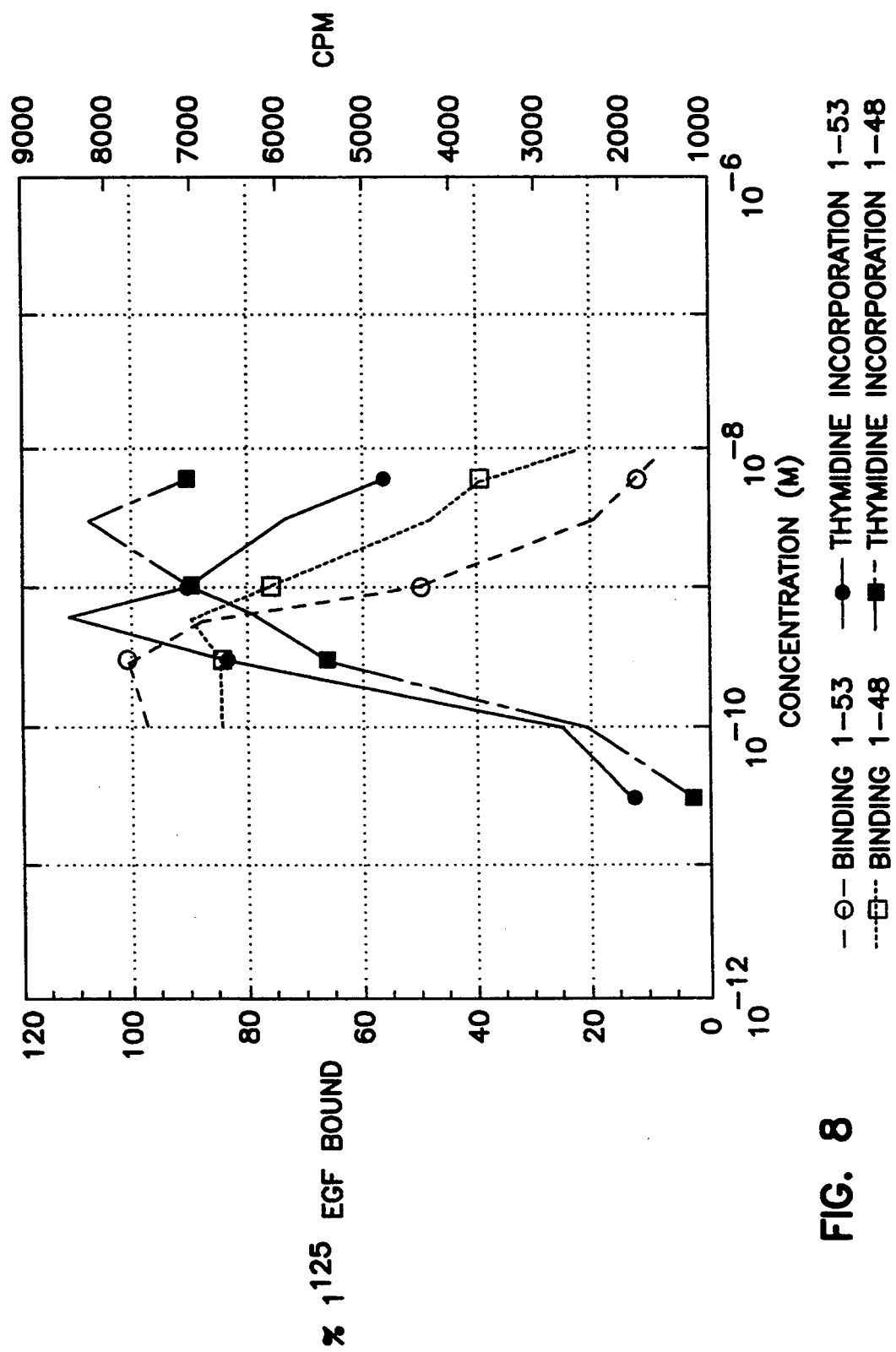
FIG. 8 is a graph showing the mitogenesis and competition binding analysis of EGF and hEGF1-48 in Balb 3T3 cells.
Figure 9:
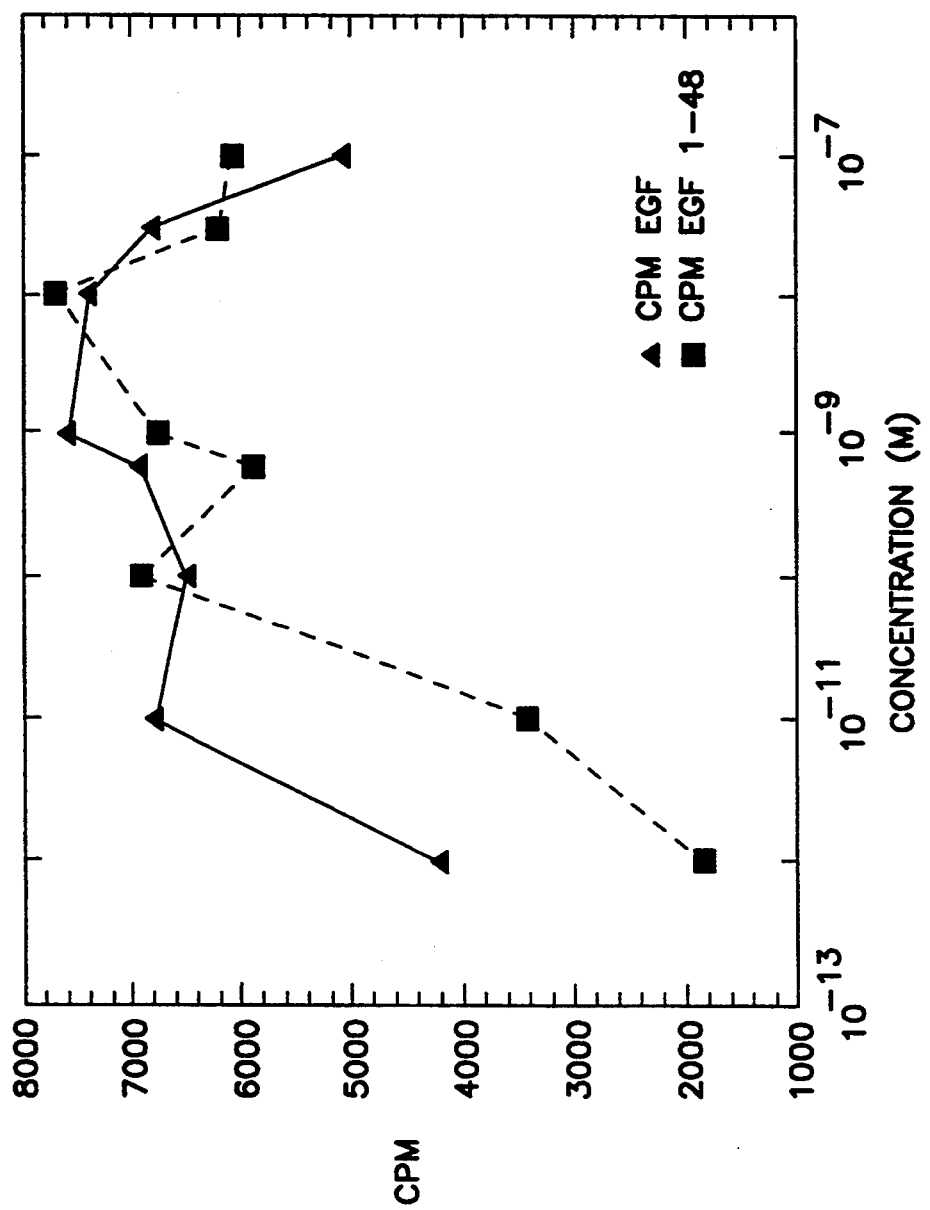
FIG. 9 is a graph showing the mitogenic effect of EGF and hEGF1-48 in NRK cells.
Figure 19:
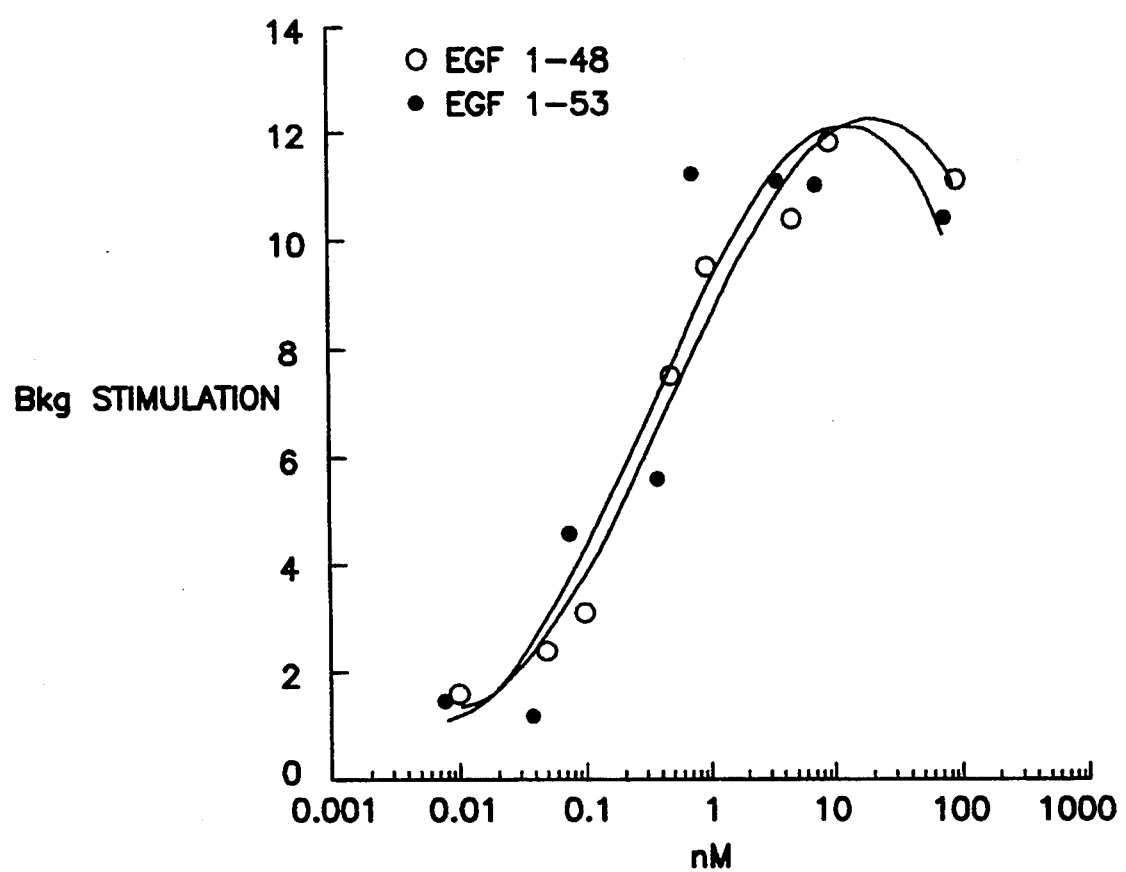
FIG. 19 is a graph showing the mitogenesis effect of EGF and hEGF1-48 in Swiss 3T3 cells.

The recombinant human EGF1-48 produced by the yeast was compared with human EGF1-53 in terms of mitogenic activity in normal rat kidney fibroblasts (NRK-49F) and two murine cell lines. The mitogenic response to EGF is cell line dependent. Maximal stimulation in the rat cell line is reached at about $10^{-11}$ M and remains unchanged up to about $10^{-8}$ M for EGF1-53. For EGF1-48, the effect is observed around $10^{-10}$ M. The mitogenic response to EGF1-53 in the murine lines occurs at a slightly different concentration and remains near maximal over a much more narrow concentration range (FIG. 8). The response to EGF1-48 in murine cell lines is about equivalent to the response to EGF1-53 except that the maximal effect occurs at slightly higher concentration and this peak effect is not diminished by increasing the EGF1-48 concentration further in contrast to the response to EGF1-53 (FIG. 8). Mitogenic evaluation using another murine cell line, CH310T1/2, was substantially similar to the Balb 3T3 data except that EGF1-48 appeared slightly more potent. Mitogenic evaluation using a different cell line Swiss 3T3 shows a similar mitogenic activity of EGF1-53 and EGF1-48 (FIG. 19). In all cell lines tested, the maximal response to EGF1-48 is at least as great as that of EGF1-53 (FIG. 8, FIG. 9).

C. Fermentation Scale-Up and hEGF Production at 250-Liter Scale

A general consideration in scale-up of fermentation processes is the relatively lower oxygen transfer capacity of larger fermentors compared to laboratory models. This consideration is especially relevant to recombinant *Pichia pastoris* expression strains. Heterologous gene expression is induced in these strains by the introduction of a methanol feed which is also used for both cell growth and metabolic energy production. Due to the highly reduced state of carbon in methanol relative to carbohydrates, methanol metabolism requires more oxygen per mole of carbon than does carbohydrate metabolism. The high oxygen requirement for methanol metabolism is often the factor that limits the rate of methanol feed, and thus limits the growth and productivity.

15-Liter Fermentation

Preliminary fermentation investigations showed, and it is a highly significant feature of the invention, that nearly quantitative conversion of hEGF to the EGF1-48 form occurred after 36 hours of methanol feed. The protocol developed for a 15-liter fermentation allowed time for complete conversion of the EGF1-52 form to hEGF1-48 by using a feed rate of 100 ml/h of methanol which filled the fermentor to 11 liters in 42 hours. A typical oxygen utilization of 33 moles $O_2$/g methanol measured in these fed batch recombinant fermentations is slightly higher than the 30 moles $O_2$/g methanol reported for continuous fermentations of wild-type *P. pastoris*. Thus, a feed rate of 100 ml/h methanol at an 8-liter volume would require an oxygen transfer rate of 330 moles $O_2$ $l^{-1}h^{-1}$. The fermentation can be adapted to fermentors with lower oxygen transfer capacity by reducing the methanol feed rate. To examine the effect of adapting to fermentors with significantly lower oxygen transfer capacity, production of hEGF1-48 was determined at methanol feed rates of 50 ml/h and 25 ml/h in the 15-liter fermentor. These reduced feed rates gave no significant differences in the amount of hEGF1-48 produced, up to about 5 grams per run. However, the time required to produce the 5 grams was 5 days longer at 25 ml/h than at 100 ml/h. Thus, the fermentation process can be readily adapted to any fermentor without loss of yield, although the productivity would be lower in fermentors with less efficient oxygen transfer.

250-Liter Fermentation

EGF production in *P. pastoris* was scaled to a 250-liter pilot plant fermentor (New Brunswick Scientific, Edison, N.J.). A proportional scale-up of the methanol feed would be 1.7 l/h; however, as anticipated, the oxygen transfer capacity initially limited the methanol feed rate to half this rate. Therefore, the operating pressure was increased from 5 to 10 psig and the air sparge was enriched with oxygen to increase oxygen transfer and allow a higher methanol feed rate. These changes allowed an increase in the methanol feed rate to 1.2 l/h. Based on the laboratory studies, the volumetric yield can be maintained at this lower feed rate by running the fermentor 18 hours longer.

From inoculation of the fermentor to harvest, the 250-liter fermentations ran 80 hours. These fermentations consumed 45 liters of methanol and allowed reproducible recovery by centrifugation of clarified broth containing 50 ±3 grams hEGF1-48. The hEGF1-48 production per liter of methanol feed was the same at the 250-liter scale as that at the laboratory scale.

D. Pilot Scale Purification

At the pilot scale (250-liter fermentor), recovery and purification of hEGF were monitored by a rapid isocratic HPLC assay for hEGF1-48. The purification was greatly simplified by the fact that hEGF1-48 is by far the predominant peptide in the broth. The HPLC profile of a sample of broth from the end of one of the 250-liter runs showed only one major peptide peak. In the initial recovery step the peptide was removed from 200 liters of clarified broth by adsorption on a reverse phase resin. The adsorption was performed stepwise in a batch mode.

After greater than 90% of the EGF was bound to reverse phase resin, the broth and resin were pumped through a column where the resin was retained by a 10μ mesh screen. The resin was washed with 0.05M acetic acid, and the EGF was then eluted from the resin with four to eight liters of eluent to effect a volume reduction from the original broth of almost two orders of magnitude. This rapid volume reduction reduces liquid handling in the later steps. After an adsorption-desorption step on a cation exchange resin to remove colored contaminants, hEGF1-48 comprised more than 85% of the total peptides as determined by analytical HPLC. The hEGF1-48 was then chromatographed by preparative HPLC, the fractions were analyzed by analytical HPLC, and the selected fractions were pooled. The HPLC was loaded with an aliquot containing 6.7 g EGF. The recovery of EGF in the fractions was 100%; the later fractions had higher purity. If the purity criteria were set much higher, for example above 99%, it is likely that the loading of the HPLC would have to be reduced in order to avoid appreciable losses in fractions which could not be pooled.

The acetonitrile introduced into the sample during the HPLC step was removed by binding the EGF to a cation exchange resin and washing with 0.05M acetic acid. This step also removed most of the trifluoroacetic acid (TFA). TFA was less than 0.1% of the final product which was lyophilized as an acetate salt. The final product obtained was the purified acetate salt of non-nicked hEGF1-48. Before lyophilization, the EGF was sterilized by filtration through a 0.2μ membrane.

The cation exchange adsorption-desorption procedure used for acetonitrile removal is the same as that which resulted in complete recovery at the decolorization step. On the basis of overall experience with this procedure, a recovery of better than 95% is normal. Thus, in routine operation at the 250-liter scale, the process described is expected to produce batches of more than 30 g of purified EGF.

EXPERIMENTAL PROCEDURES

A. EGF Production Strains

Three different recombinant strains of *P. pastoris* were tested for the production of hEGF. Two strains, as indicated, contained respectively two and four, respectively, copies of an hEGF expression cassette coding for EGF1-53 integrated into the AOX1 locus of the host strain GS115. A third strain G+EGF206S10 contains six copies of an hEGF cassette coding for EGF1-48 integrated at the HIS4 locus of the host strain GS115. Each expression cassette contains the *P. pastoris* alcohol oxidase AOX1 promoter, and regulatory sequences, DNA sequences coding for the *S. cerevisiae* α-mating factor prepro leader sequence fused to a synthetic gene encoding respectively for hEGF1-53, hEGF1-53 and EGF1-48 (FIG. 7), and the AOX1 transcription termination sequence. The transforming DNA also includes the *P. pastoris* HIS4 sequence.

Recombinant hEGF-producing strains of *P. pastoris* were developed by transformation of the auxotrophic His-Pichia host strain GS115 with vectors containing two, five or six hEGF expression cassettes. The expression vector comprised of two hEGF1-53 expression cassettes, as indicated, is pAO817, and that having five hEGF1-53 cassettes is pEGF819. An expression vector comprised of six hEGF1-48 cassettes is called pEGF206.

*Pichia pastoris* strain GS115 was the host for transformation with these vectors.

Deposit of Cultures

Viable cultures of the *P. pastoris* strain GS115 were deposited, under the terms of the Budapest Treaty at the American Type Culture Collection, Rockville, Md. USA ("ATCC") on Aug. 15, 1987 and were assigned ATCC Accession No. 20864, as documented by PCT Patent Publication No. WO 90/03431, Pub. Date, 5 Apr. 1990, incorporated herewith by reference. Undigested vectors pAO817 and pEGF819 and linearized vector pEGF206 were transformed into GS115 by the spheroplast method [Cregg et al., *Mol. Cell. Biol.* 5, 3376–3385 (1985) incorporated herewith by reference]. After selection and analysis by Southern hybridization, the following strains were identified: strain G+EGF817S1 contains two copies of the hEGF1-53-encoding cassette integrated at the AOX1 locus; strain G+EGF819S4 contains four copies of the hEGF1-53-encoding cassette (one copy was lost from the five-copy plasmid vector by recombination during transformation) integrated at the AOX1 locus, and strain G+EGF206S10 contains six copies of the hEGF1-48-encoding cassette integrated at the HIS4 locus.

B. Fermentation Protocols

Fifteen-liter fermentations (in a 15-liter Biolafitte fermentor) were started in a six-liter volume containing four liters of basal salts [52 ml/l 85% phosphoric acid, 1.8 g/l calcium sulfate.2H$_2$O, 28.6 g/l potassium sulfate, 23.4 g/l magnesium sulfate.7H$_2$O, 6.5 g/l potassium hydroxide] and 400 g of glycerol. After sterilization, 25 ml of PTM$_1$ trace salts solution [6.0 g/l cuptic sulfate.5-H$_2$O, 0.08 g/l sodium iodide, 3.0 g/l manganese sulfate.H$_2$O, 0.2 g/l sodium molybdate.2H$_2$O, 20 g/l zinc chloride, 0.02 g/l boric acid, 0.5 g/l cobalt chloride, 65.0 g/l ferrous sulfate.7H$_2$O, 0.2 g/l biotin and 5.0 ml/l sulfuric acid (conc)] were added, and the pH was adjusted and subsequently maintained at 5.0 by the addition of ammonia gas throughout the fermentation. Excessive foaming was controlled by the addition of 5% Struktol J673 antifoam. The fermentor was inoculated with a volume of 500 ml of an overnight culture (OD$_{600}$=1 to 4) of the EGF-expressing strain in Yeast Nitrogen Base (YNB), 2% glycerol, 0.1M potassium phosphate, pH 6. The dissolved oxygen was maintained above 20% by increasing the air flow rate up to 20 liter/minute, the agitation up to 1000 rpm and/or the pressure of the fermentor up to 1.5 bar during the fermentation.

After exhaustion of the initial glycerol charge, a 50% glycerol feed, containing 12 ml/l PTM$_1$ trace salts, was initiated at a rate of 120 ml/h; the glycerol feed continued for 6 hours, at which time the methanol feed, 100% methanol plus 12 ml/lPTM$_1$ trace salts, was started at a rate of 20 ml/h. The methanol feed was increased by 10% each half hour until a feed rate of 100 ml/h was reached. The fermentation was then continued for 25-35 hours.

The conditions for 2-liter and 250-liter fermentors were scaled proportionately from the 15-liter fermentor, except that the final methanol feed rate was limited to the highest rate at which the dissolved oxygen concentration could be maintained above 20% air saturation. In the 2-liter and 250-liter fermentors, the pH was controlled with NH$_4$OH rather than NH$_3$, and in the 250-liter fermentor, the air sparge was supplemented with O$_2$ in some runs.

C. Analytical HPLC

Broth samples to be assayed by HPLC were treated by centrifugation for three minutes in a microcentrifuge to remove cells. Reverse phase HPLC was performed on a Waters Bondapak C18 (0.25×30 cm) column with a C18 guard column. Mobile Phase A consisted of 0.1% by weight TFA in deionized water, and Mobile Phase B was 95% acetonitrile/5% H$_2$O with 0.1% TFA. The column was equilibrated with a mixture of 80% A and 20% B at a flow rate of 1 ml/min. for 20 minutes before each run.

Each analytical run was 50 minutes. The first five minutes were isocratic at 80% A, 20% B; then the concentration of B was increased linearly over the next 25 minutes to 30% B; and, finally the concentration of B was increased linearly to 55% during the final 20 minutes. UV absorbance was monitored at 210 nm. The different HPLC systems used at several sites gave comparable results.

A shorter analytical HPLC procedure was developed for process control at the pilot scale. The shorter procedure consisted of a ten minute run at isocratic conditions of 72% A, 28% B.

D. Analytical Mass Spectometry

Figure 13:
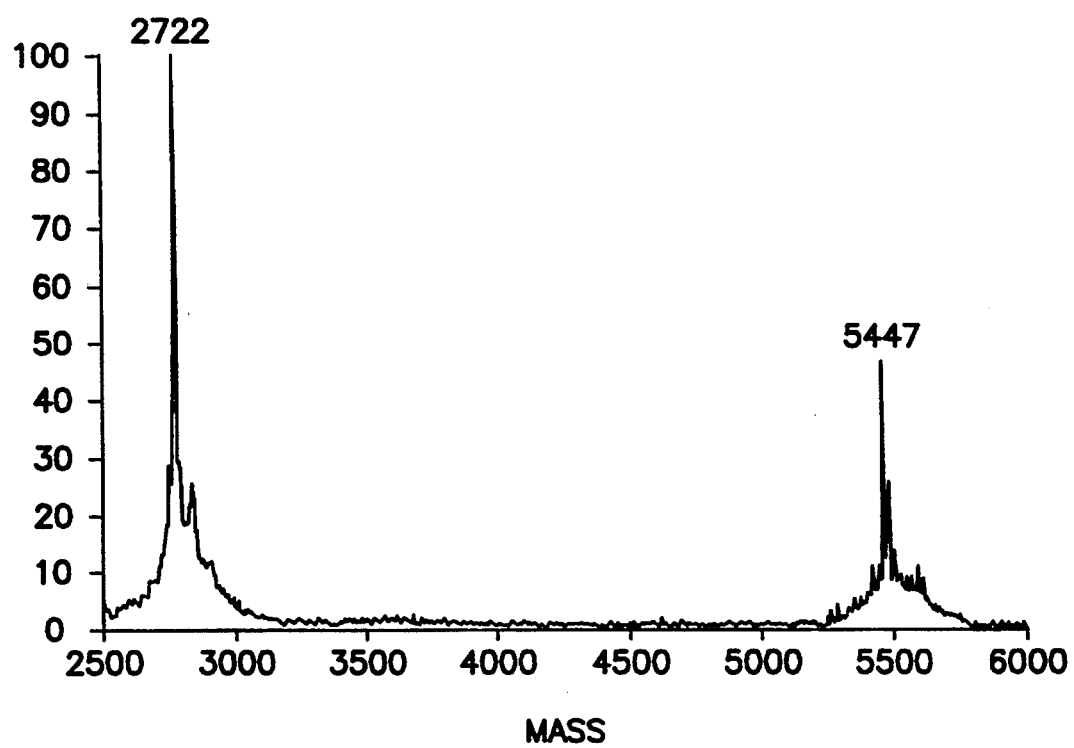
FIG. 13 represents the FAB Mass Spectroscopy of hEGF1-48 including the half-ion moiety, with peaks at 2722 and 5443.
Figure 14:
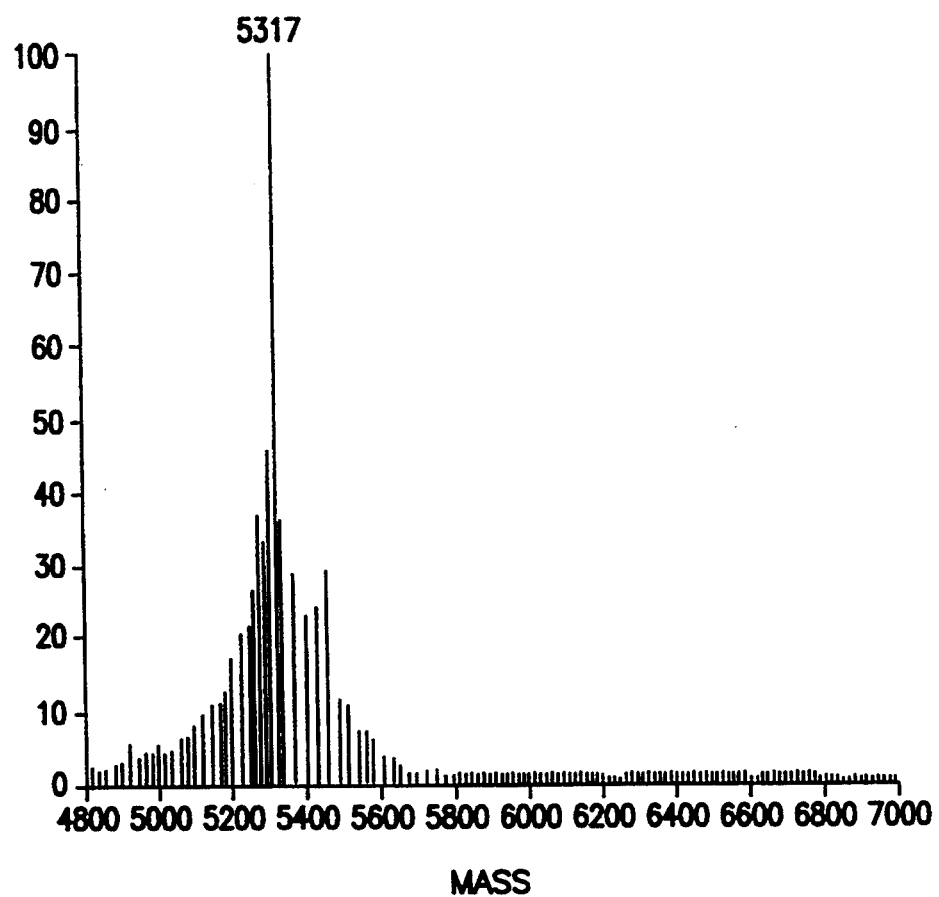
FIG. 14 represents the FAB Mass Spectroscopy of hEGF1-47 with a peak at 5317.
Figure 15:
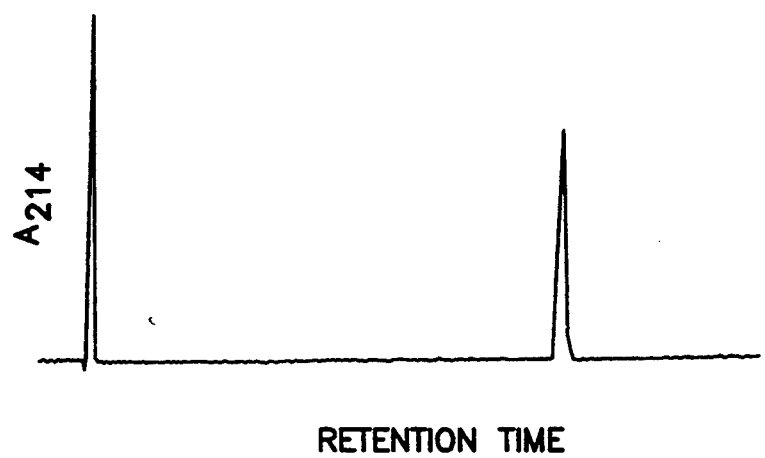
FIG. 15 is a chromatogram of reverse phase chromatography (RPC) of a purified fraction of hEGF1-47.
Figure 16:
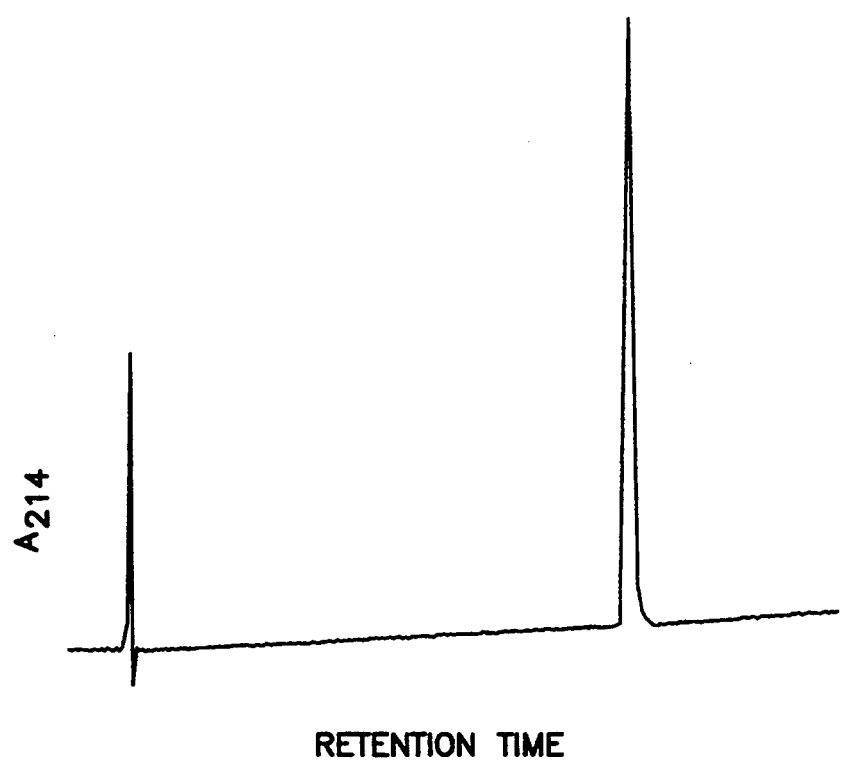
FIG. 16 is a chromatogram of reverse phase chromatography (RPC) of a purified fraction of hEGF1-49.
Figure 17:
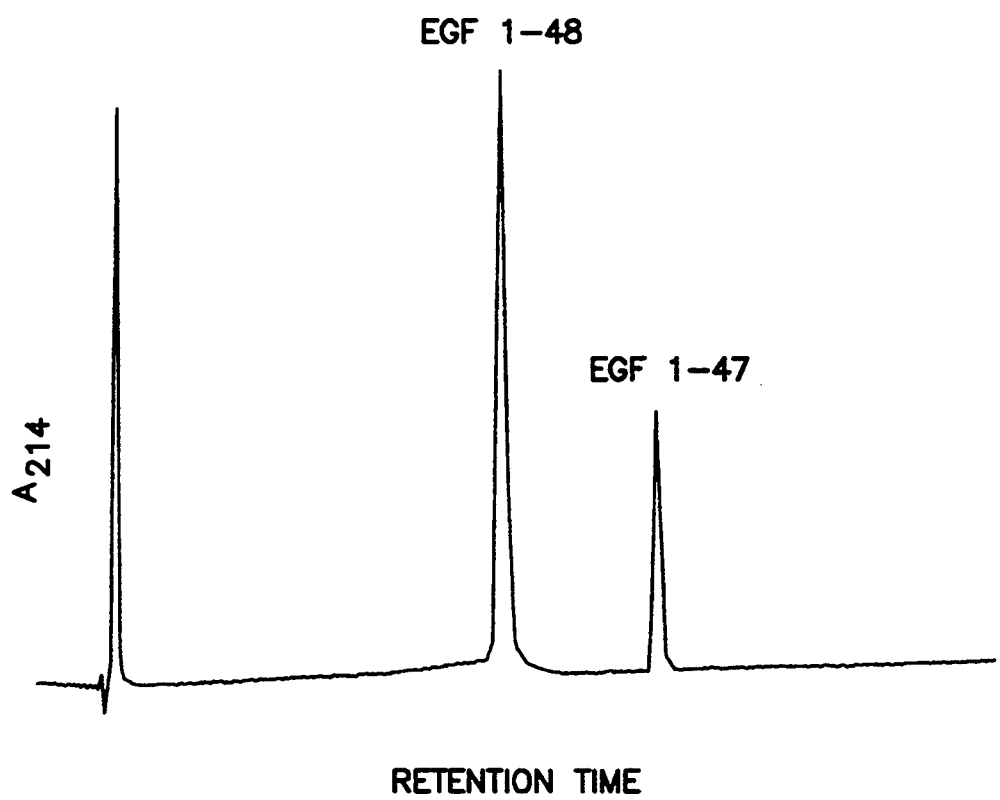
FIG. 17 is a co-chromatogram of RPC of a mixture of hEGF1-48 and EGF1-47 prepared from purified Fractions of the individual species with peaks at 12.83 and 17.16.
Figure 18A:
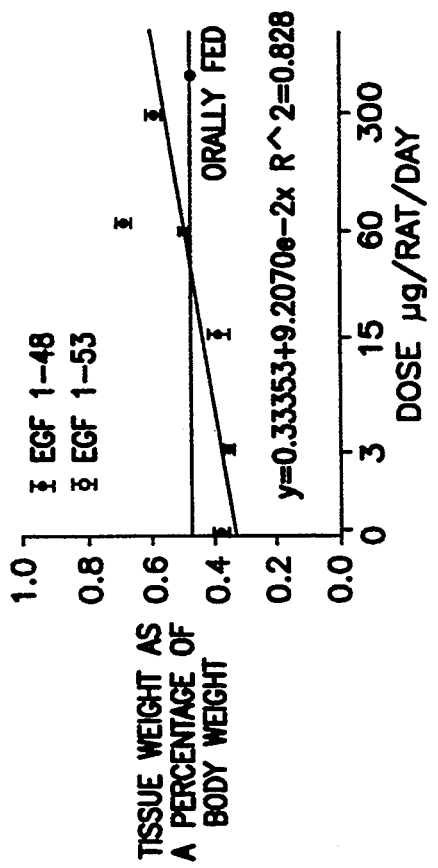
FIG. 18 is a series of plots (for the stomach, caecum, small intestine, and colon) showing the dose-response effects of hEGF on GI cell proliferation at various IV doses in the rat.
Figure 18B:
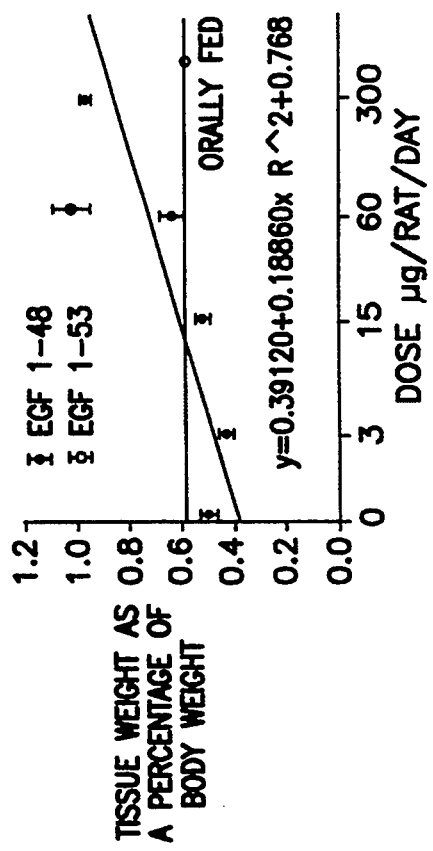
Figure 18C:
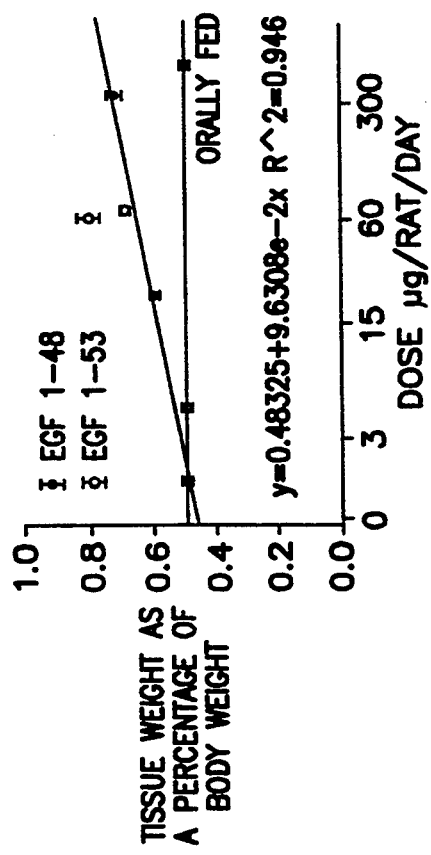
Figure 18D:
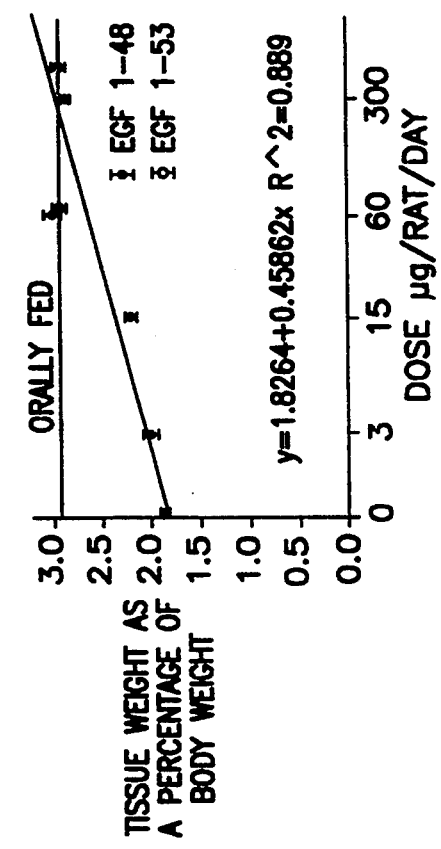

Small amounts of EGF1-47, EGF1-48, EGF1-51, and EGF1-52 were purified from the fermentation broth by reverse phase HPLC; see FIGS. 15, 16 and 17. These purified samples were analyzed by fast atom bombardment (FAB) mass spectometry; see FIGS. 13 and 14.

E. Bioactivity Assays

Mitogenic (i.e., cell replication) stimulation by hEGF1-48 was determined in three cell lines by tritiated thymidine uptake. Murine Balb 3T3 cells, C3H1OT1/2 cells, and normal rat kidney fibroblasts (NRK-49F) cells were plated into 24 well plates in DMEM (4.5 g/l glucose), phenol red-free, containing 5% Colorado calf serum (Colorado Serum Company). Cells were grown at 37° C. in 5% CO$_2$ atmosphere. The medium was changed every three days. Cells reached confluence in about three to four days and were allowed to remain at confluence for 24-48 hours before assay. The medium was removed and replaced with DMEM containing 0.1% BSA (Sigma) and 10 U/ml penicillin/streptomycin (Gibco). The cells were serum starved for 22 hours, after which EGF1-53 and EGF1-48 were added in the dose range 0.0 to 30.0, for 24 hours, Dilutions were made from a stock solution of each EGF species whose concentration was determined by amino acid analysis. For maximal stimulation, cells were incubated with 5% calf serum. After the 24 hour incubation period, 100,000 cpm/well of [3H]Thymidine (Amersham) were added, and the plates were incubated at 34° C. for 90 minutes. The cells were then washed with 1.5 ml cold PBS, followed by a 20 minute incubation at 4° C. with 1 ml cold fixative (50% methanol, 10% acetic acid and 40% PBS). Fixative was aspired off and replaced with 0.4 ml of 1% SDS. The plates were placed on an orbital shaker for about 15 minutes or until the cells detached. The cell suspension was then transferred to scintillation vials and 10 ml scintillation fluid (ScintiVerse BD, Fisher Scientific) were added. Vials were vortexed and placed in a beta counter (LKB 1219, Rackbeta). By these assays intact hEGF1-48 had mitogenic activity comparable to that of hEGF1-53. The mitogenic activity of hEGF1-48, using a slightly different protocol, was also confirmed in the Swiss 3T3 cell line (FIG. 19).

F. Purification Protocols at 250-Liter Scale

Human EGF-containing broth was separated from cells by centrifugation at a 3 LPM feed rate and 40 second shoot time (i.e., 40 second interval between discharges) in an Alfa-Laval BTPX205 stacked disc, intermittent discharge, continuous centrifuge at approximately 13,000×g. The cell concentrate was diluted with deionized water to its original volume and centrifuged as before. The clarified broths from the two separations were combined and further clarified by centrifuging again at a 6 LPM feed rate with a 20 minute shoot time.

Human EGF was removed from the resulting broth by step-wise addition of a reverse phase resin that had been wetted in two volumes methanol (ml/g). Two aliquots of 200 g each (300 g in Run 1), and subsequent aliquots of 300 g each of Vydac 281TPB 15-20 were added to the broth, and the mix was stirred for 15 minutes after each addition. Subsequent to each resin addition, the amount of unbound EGF remaining in the broth was measured by the shorter analytical HPLC procedure. Additional aliquots of resin were added until less than 10% of the starting EGF remained unbound.

The resin was separated from the broth by pumping the resin-broth mixture through a column (30-cm diameter, Amicon) with a 10μ mesh screen on the bottom support; the top screen was removed prior to the procedure. After the broth was passed through the column, the top screen was replaced, and the resin was washed with 0.05M acetic acid. The EGF was then eluted with two 4-liter aliquots of 38% ethanol acidified with 3 ml/l glacial acetic acid. The eluate was decolored by loading an aliquot containing not more than 25 g EGF into a column containing six liters of cation exchange resin (Macrosorb KAX-CM Resin, Sterling Organics) equilibrated in 0.06 mM acetic acid. The EGF was then eluted from the column with 12 liters of 0.3M ammonium acetate and the column regenerated, as recommended by the manufacturer, with 1M sodium acetate and 0.1M sodium hydroxide before decolorizing additional aliquots.

Aliquots of the eluate from the cation exchange column containing not more than 8 g EGF each were loaded onto a two-inch diameter radial compression Waters C18 column for preparative HPLC (Waters Delta prep, Model 3000). The column was washed with a mixture of nine parts A and one part B (90% A, 10% B, the same composition as described for analytical HPLC); EGF was eluted in a 40-minute linear gradient, increasing B from 10% to 25%. Samples (40 ml) were collected from 15 minutes to 30 minutes, and EGF purity was assessed by analytical HPLC. Samples were selected and pooled to give a final purity greater than 95%. To remove acetonitrile, the pooled fractions were loaded onto a 6-liter cation exchange column (Macrosorb KAX-CM resin), and washed with 0.05M acetic acid until the acetonitrile concentration in the effluent was below 10 ppm, as determined by gas chromatography. EGF was eluted with 0.3M ammonium acetate. The eluate was filtered through a 0.2μ filter and lyophilized to a final moisture content of 8%. The product obtained was pure non-nicked hEGF1-48.

The description shows in detail means for producing hEGF and especially hEGF1-48 in pure non-nicked form.

Effect of IV hEGF1-48 on Gastric Acid Secretion in Monkeys

Five female Rhesus monkeys (5.5–10.2 kg) were used for these experiments. In all the experiments described below, gastric acid secretion was stimulated by continuous IV infusion of histamine (200 μg/kg iv). Two hours after initiation of histamine infusion, the animals received an IV injection of non-nicked hEGF1-48. Gastric secretion was collected continuously through a naso-gastric tubing placed in the dependent portion of the stomach and collected in 30-min fractions. The volume and pH of the fractions were measured and an aliquot titrated to pH 7 with NaOH. Hydrogen ion concentration and gastric acid output were calculated.

Figure 10:
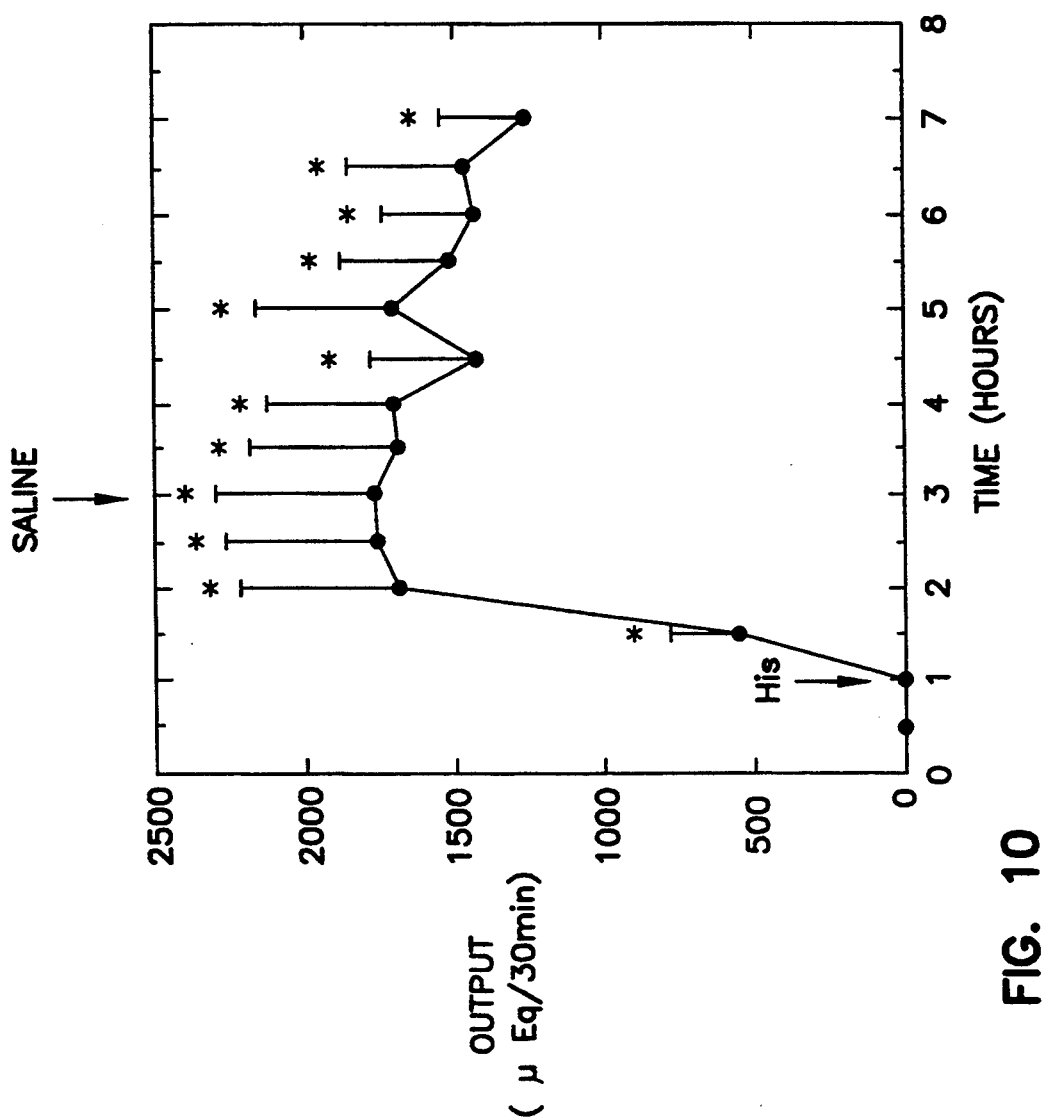
FIG. 10 is a graph showing the histamine-stimulated gastric output in monkeys over time (hours) versus saline controls.
Figure 11A:
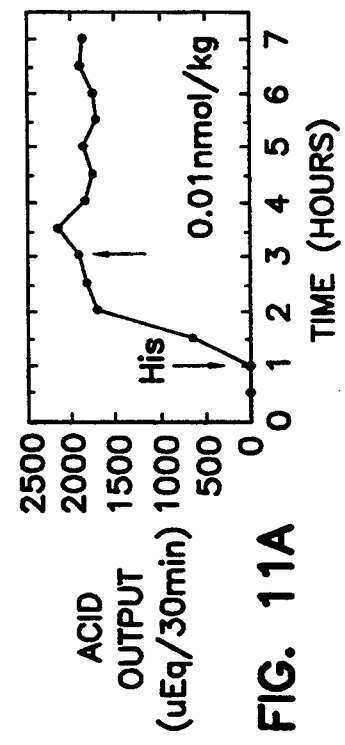
FIG. 11 is a series of graphs showing the time course effect of intravenous hEGF1-48 at graded doses on histamine-stimulated gastric acid output in monkeys.
Figure 11B:
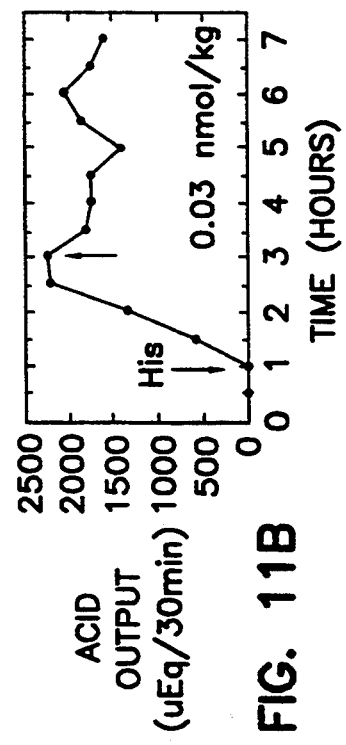
Figure 11C:
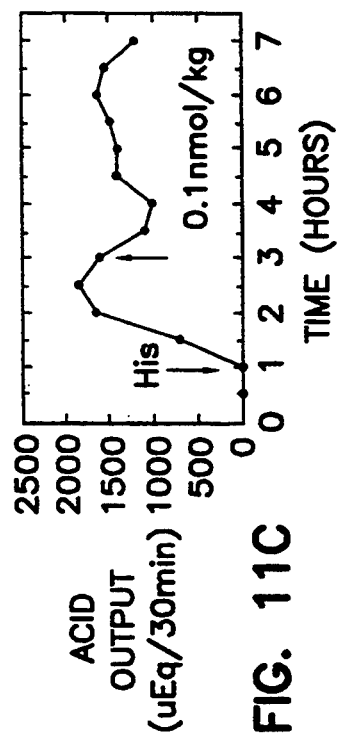
Figure 11D:
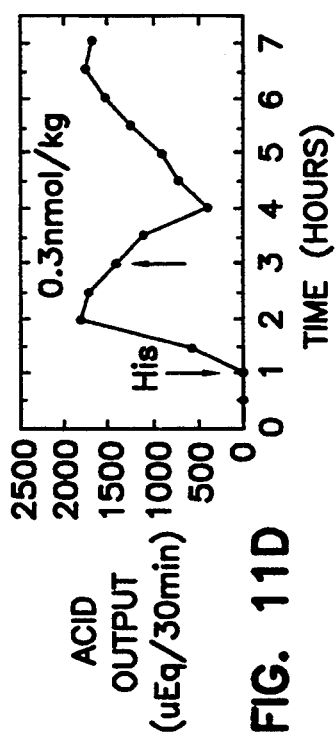
Figure 11E:
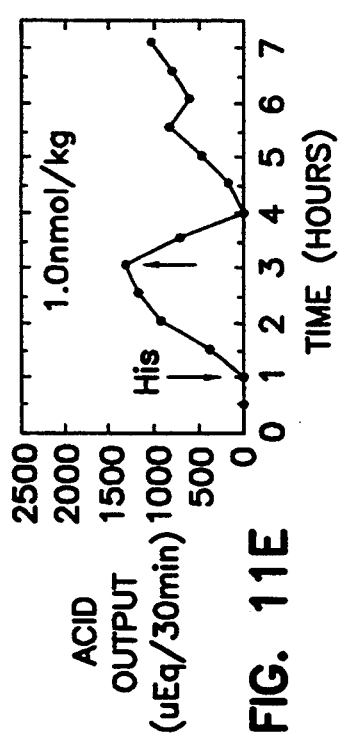
Figure 11F:
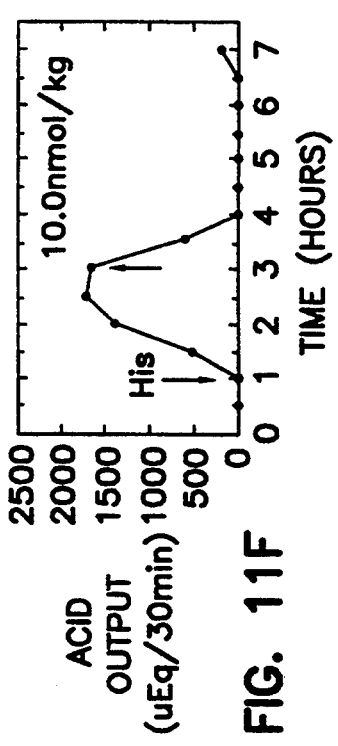

As shown in FIG. 10, histamine potently stimulates gastric acid output in the monkey. The gastric acid output reached a peak about 1 hour after drug infusion and remained constant over a period of several hours.

hEGF1-48 injected IV dose-dependently inhibited histamine-stimulated gastric acid output (FIG. 11). An almost complete inhibition was observed 60 minutes after IV administration of 1 and 10 nmol/kg hEGF1-48.

Figure 12:
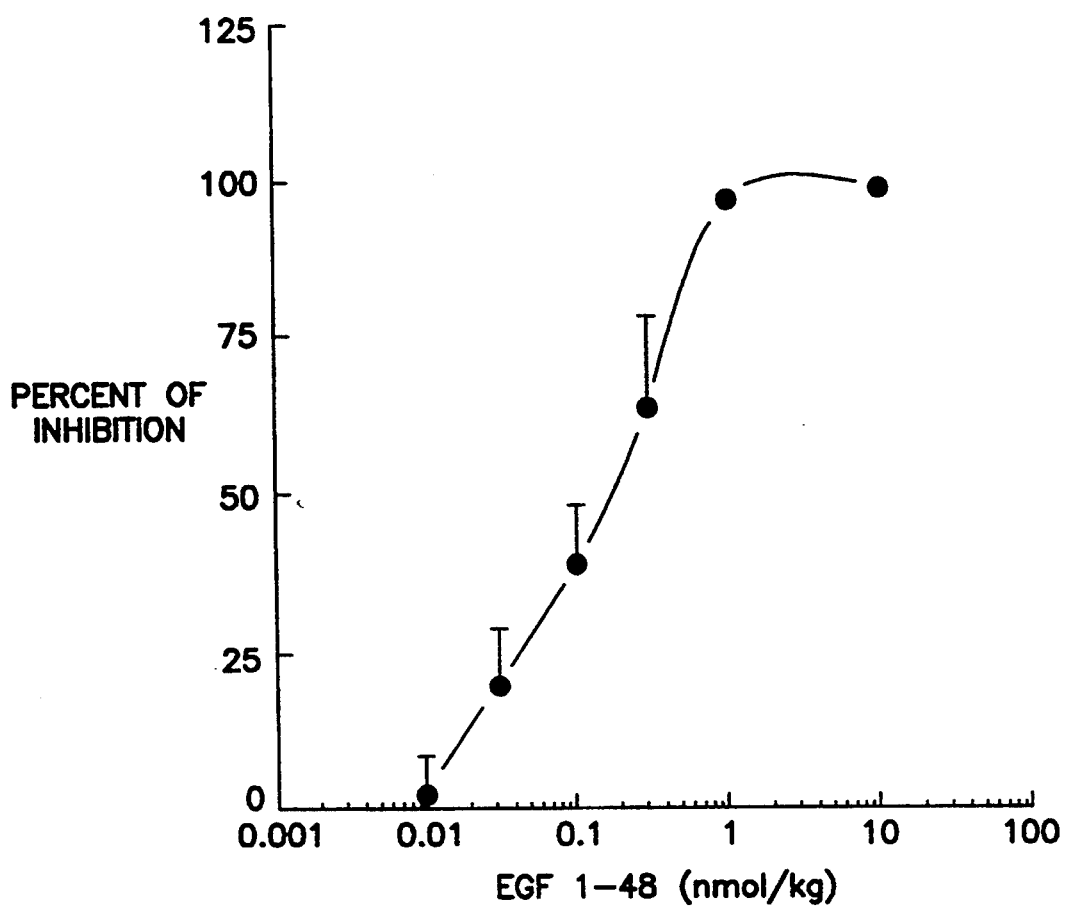
FIG. 12 is a dose-response plot of the percent inhibition of histamine-induced stimulation of gastric acid output in the monkey one hour after intravenous administration of hEGF1-48.

The percent of inhibition of hEGF1-48 on histamine-stimulated gastric acid output measured 60 minutes after IV administration of the drug is shown in FIG. 12. A dose of 0.03 nmol/kg induced a 20% inhibition of gastric acid output while 96.9% and 99.0% inhibition of gastric acid output were observed after administration of 1 and 10 nmol/kg respectively. These data show that intravenous hEGF1-48 dose-dependently inhibits histamine stimulation of gastric acid secretion, the ED50 is equal to 0.2 nmol/kg, and an almost complete inhibition is achieved within 1 hour after IV administration of the drug.

Dose-Response Effect of IV hEGF1-48 On GI Cell Proliferation in the Rat

Male 200 g Wistar rats were housed individually in wire bottomed Perspex cages. The right external jugular vein was cannulated (under anaesthesia) with a silastic catheter, which was brought round to the back of the neck by a skin tunnel, and connected via a Harvard skin button and stainless steel tether to a Harvard miniature fluid swivel joint. Each rat was infused with 60 ml/day of the intravenous diet. Recombinant EGF1-48 was added to the diet.

At the end of the experiment the rats were given 1 mg/kg vincristine sulphate intravenously, and killed, at time intervals. Intestinal samples were weighed and fixed in Carnoy's fluid. The tissue was stained by the Feulgen reaction and the antral glands, intestinal crypts or colonic crypts were microdissected; the number of arrested metaphases in ten crypts was counted. For some studies the accumulation of metaphases over a two hour period was counted to give an augmented mitotic index, while for other investigations the rate of accumulation of arrested metaphases over a three hour period was calculated to give the crypt cell production rate.

The results of cell proliferation (in the stomach, caecum, small intestine, and colon) as measured by increase in organ tissue weight (as % body weight) is shown in FIG. 18.

The invention has been described in detail with respect to particular embodiments thereof, but reasonable variations and modifications, within the spirit and scope of the present disclosure, are contemplated by the present disclosure and the appended claims.

REFERENCES

1. Cohen, S. Isolation of a mouse submaxillary gland protein accelerating incisor eruption and eyelid opening in the newborn animal. *J. Biol. Chem.* 237: 1555–1562 (1962).
2. Cohen, S. Epidermal growth factor. *J. Invest. Dermatol.* 59: 13–16 (1972).
3. Cohen, S. and G. Carpenter. Human epidermal growth factor: Isolation and chemical and biological properties. *Proc. Natl. Acad. Sci. U.S.A.* 72: 1317–1321 (1975).
4. Gregory, H. Isolation and structure of urogastrone and its relationship to epidermal growth factor. *Nature (London)* 257: 325–327 (1975).

5. Gregory, H. and B. M. Preston. The primary structure of human urogastrone. *Int. J. Peptide Protein Res.* 9: 107–118 (1977).
6. Gregory, H. and I. R. Willshire. The isolation of the urogastrones-inhibitors of gastric acid secretion from human urine. *Hoppe-Seylers Z. Physiol. Chem.* 356: 1765–1774 (1975).
7. Carpenter, G. The regulation of cell proliferation: Advances in the biology of action of epidermal growth factor. *J. Invest. Dermatol.* 71:283–288 (1978).
8. Hollenberg, M. D. Epidermal growth factor-urogastrone: A polypeptide acquiring hormonal status. *Vitamins Hormones* 37: 69–110 (1979).

We claim:

1. A non-nicked polypeptide hEGF1-48 or a pharmaceutically acceptable salt thereof.

2. A trifluoroacetate salt or acetate salt of the non-nicked EGF1-48 of claim 1.

3. A pharmaceutical composition in dosage form for management or treatment of diseases of the gastrointestinal mucosa including erosive and inflammatory diseases, comprising a pharmaceutically effective amount of a polypeptide as in claim 1 and a pharmaceutically acceptable carrier.

4. A method for management or treatment of diseases of the gastrointestinal mucosa including erosive and inflammatory diseases in a subject which comprises administering to the subject non-nicked hEGF1-48 or a pharmaceutically acceptable salt thereof in an amount pharmaceutically effective to manage the disease in the subject or to promote the management or healing thereof.

5. A method according to claim 4 wherein the non-nicked EGF1-48 is administered for human therapy in an oral dosage regimen as a salt or non-salt in pharmacologic amounts between about 0.001 to about 100 nanomoles per kilogram per day.

6. A method according to claim 4 where the treatment comprises administering to a human the non-nicked EGF1-48 as the acetate salt thereof.

* * * * *

UNITED STATES PATENT AND TRADEMARK OFFICE
CERTIFICATE OF CORRECTION

PATENT NO. : 5,434,135
DATED : July 18, 1995
INVENTOR(S) : Parikh et al.

It is certified that error appears in the above-identified patent and that said Letters Patent is hereby corrected as shown below:

On column 5, line 25, please delete "25position" and substitute therefore --25-26 position--

On column 5, line 31, please delete "hEGE1-53" and substitute therefore --hEGF1-53--

On column 6, line 33, please delete "pharmocogically" and substitute therefore --pharmacologically--

On column 7, line 29, please delete "vital" and substitute therefore --viral--

On column 8, line 7, please delete "pit6" and substitute therefore --pH6--

On column 10, line 29, please insert --3%-- after the word "to"

On column 15, line 15, please delete "cuptic" and substitute therefore --cupric--

Signed and Sealed this

Second Day of January, 1996

*Attest:*

BRUCE LEHMAN

*Attesting Officer*     Commissioner of Patents and Trademarks